United States Patent
Buss

(10) Patent No.: US 11,310,970 B2
(45) Date of Patent: Apr. 26, 2022

(54) METHOD OF DETERMINATION OF WATER STRESS IN A ONE OR MORE PLANTS IN A CROP LOCATED IN THE VICINITY OF A SOIL MOISTURE SENSOR ARRAY AND KNOWLEDGE OF ETO

(71) Applicant: Sentek Pty Ltd, South Australia (AU)

(72) Inventor: Peter Buss, South Australia (AU)

(73) Assignee: SENTEK PTY LTD, Stepney (AU)

( * ) Notice: Subject to any disclaimer, the term of this patent is extended or adjusted under 35 U.S.C. 154(b) by 0 days.

(21) Appl. No.: 16/639,853

(22) PCT Filed: Aug. 22, 2018

(86) PCT No.: PCT/AU2018/000145
§ 371 (c)(1),
(2) Date: Feb. 18, 2020

(87) PCT Pub. No.: WO2019/036744
PCT Pub. Date: Feb. 28, 2019

(65) Prior Publication Data
US 2020/0359583 A1    Nov. 19, 2020

(30) Foreign Application Priority Data

Aug. 22, 2017   (AU) ................................ 2017903385

(51) Int. Cl.
*A01G 25/16*    (2006.01)
*G01N 33/24*    (2006.01)

(52) U.S. Cl.
CPC ......... *A01G 25/167* (2013.01); *A01G 25/165* (2013.01); *G01N 33/246* (2013.01)

(58) Field of Classification Search
CPC .... A01G 25/167; A01G 25/165; A01G 25/16; G01N 33/246
See application file for complete search history.

(56) References Cited

U.S. PATENT DOCUMENTS

| 5,418,466 A | 5/1995 | Watson et al. |
| 7,042,234 B2 | 5/2006 | Buss |

(Continued)

FOREIGN PATENT DOCUMENTS

| AU | 760525 B2 | 5/2003 |
| AU | 20020331464 B2 | 6/2014 |
| WO | 2014165910 A1 | 6/2007 |

OTHER PUBLICATIONS

International Search Report and Written Opinion for International Application No. PCT/AU2018/000145, dated Feb. 28, 2019, 7 pages.

(Continued)

*Primary Examiner* — Chad G Erdman
(74) *Attorney, Agent, or Firm* — Westman, Champlin & Koehler, P.A.

(57) ABSTRACT

Crops for human and animal consumption of many types are well known by their respective growers. Years of experience in the field provide the grower knowledge about a range of conditions that lead to the full spectrum of crop yields and crop quality, and each grower creates a store of knowledge which they can combine with the available measures of those conditions. This disclosure provides a method for indicating the onset of water stress in one or more plants located in a soil the roots of which are within the measurement zone of a soil moisture sensor located in the soil, by determining if there was no recorded water into soil event in the prior 24 hour period of a respective one 24 hour period; determining from representative data whether there are two respective 24 hour periods of the prior seven consecutive 24 hour periods also have evapotranspiration values within a predetermined range; determining from representative data the rate of soil moisture depletion during the plant moisture uptake period within each respective 24 hour period adjusted for drainage; determining whether the rate of soil moisture (Continued)

Saturation

"Field Capacity"

Permanent Wilting Point depletion during the plant moisture uptake period within each respective 24 hour period reduces by a pre-determined level compared to the other of the respective 24 hour period; and indicating the most recent of the respective two 24 hour periods as a period of water stress of the one or more plants.

3 Claims, 22 Drawing Sheets

(56) References Cited

U.S. PATENT DOCUMENTS

| | | |
|---|---|---|
| 7,240,743 B2 | 7/2007 | Buss et al. |
| 9,894,849 B2 * | 2/2018 | Rooney .................. A01G 25/02 |
| 2009/0177330 A1 | 7/2009 | Kah, Jr. |
| 2015/0061888 A1 | 3/2015 | Lankford et al. |
| 2015/0181817 A1 | 7/2015 | Runge et al. |
| 2018/0129175 A1 * | 5/2018 | Jennings ............ G06K 9/00657 |

OTHER PUBLICATIONS

B. Venkateswarlu et al. (eds), Crop Stress and its Management: Perspectives and Strategies, DOI 10.007/978-94-007-2220-0_3, Springer Science+Business Media B.V. 2012, Author K.K. Vinod, Chapter 3: "Stress in Plantation Crops: Adaption and Management," 48 pages.
Extended European search report for European patent application No. 18848232.7, dated Apr. 28, 2021, 3 pages.

* cited by examiner

South Australia Daily Evaptranspiration

| Location | Evapotrans-piration (mm) 0000-2400 | Rain (mm) 0900-0900 | Pan Evaporation (mm) 0900-0900 | Max Temp | Min Temp | Max Rel Hum (%) | Max Rel Hum (%) | Average 10m Wind Speed (m/sec) | Solar Radiation (MJ/sq m) |
|---|---|---|---|---|---|---|---|---|---|
| Adelaide (Kent Town) | 5.9 | 0.0 | | 26.0 | 9.7 | 84 | 27 | 1.99 | 32.00 |
| Adelaide Airport | 5.4 | 0.0 | 10.0 | 22.7 | 8.5 | 89 | 46 | 3.80 | 31.78 |
| Cape Borda | 5.1 | 0.0 | | 20.1 | 7.2 | 88 | 49 | 5.56 | 31.84 |
| Cape Jaffa (The Limestone) | 3.9 | 0.0 | | 18.5 | 11.7 | 84 | 55 | 3.22 | 21.89 |
| Cape Willoughby | 5.0 | 0.0 | | 18.8 | 13.1 | 75 | 57 | 4.90 | 30.35 |
| Ceduna Amo | 7.7 | 0.0 | | 30.3 | 4.7 | 95 | 19 | 4.31 | 31.43 |
| Clare High School | 6.2 | 0.0 | | 26.9 | 8.1 | 85 | 19 | 2.59 | 30.04 |
| Cleve Aerodrome | 6.2 | 0.0 | | 24.9 | 8.9 | 95 | 36 | 4.88 | 31.15 |
| Coober Pedy Airport | 9.4 | 0.0 | | 32.1 | 16.3 | 39 | 8 | 4.56 | 31.69 |
| Coonawarra | 3.0 | 0.2 | | 18.1 | 11.0 | 92 | 52 | 2.74 | 15.18 |
| Coulta (Coles Point) | 5.9 | 0.0 | | 24.9 | 11.6 | 82 | 35 | 4.39 | 26.42 |
| Cummins Aero | 6.4 | 0.0 | | 27.2 | 10.4 | 91 | 29 | 4.35 | 27.69 |

*Figure 7*

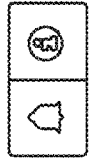
*Figure 9*

METHOD OF DETERMINATION OF WATER STRESS IN A ONE OR MORE PLANTS IN A CROP LOCATED IN THE VICINITY OF A SOIL MOISTURE SENSOR ARRAY AND KNOWLEDGE OF ETO

CROSS-REFERENCE TO RELATED APPLICATION

This application is a Section 371 National Stage Application of International Application No. PCT/AU2018/000145, filed 22 Aug. 2018 and published as WO 2019/036744 A1 on 28 Feb. 2019, in English, the content of which is incorporated by reference.

FIELD

The field of the disclosure is crop stress determination.

INCORPORATION BY REFERENCE

The field of soil characteristics measurement and in particular soil moisture and salinity is described in various published patents and patent applications owned by the subject applicant, including U.S. Pat. No. 5,418,466; AU760525; AU20020331464; U.S. Pat. Nos. 7,042,234; and 7,240,743, WO2014/165910 all of which are incorporated by reference into this specification.

BACKGROUND

Crops for human and animal consumption of many types are well known by their respective growers. Years of experience in the field provide the grower knowledge about a range of conditions that lead to the full spectrum of crop yields and crop quality, and each grower creates a store of knowledge which they can combine with the available measures of those conditions (rainfall, soil saturation and thus water logging stress, air temperature, sunshine periods, wind speed and direction, watering quantity and timing, soil treatment/s and condition, insects, weed type and density, pests, pathogens (viruses and other microbes), birds, atmospheric gases, etc. indeed multiple stressors can work individually and concurrently) to correlate the different yields, plant quality, plant health and growth patterns that result from one or more of the related conditions.

The pressure on growers to use that knowledge to consistently produce ever higher quality and ever higher crop yields mounts as the cost of the crop establishment and growing inputs increase and the return for the harvested crop varies with demand and supply.

It could be said however, that most growers learn when crops have been water stressed well after the stress has occurred since they see a reduction in quality and yield at the time of harvest, or see that the health of the crop plant/plants is suffering as evidenced by leaf or fruit changes, all of which are lagging indicators of the crop having endured stress to some degree at an earlier time.

There is a need for a tool to identify water stress closer in time than prior indications have indicated stress in a crop.

BRIEF DESCRIPTION OF ASPECTS OF THE DISCLOSURE

This disclosure relates to a method for the determination of water stress in a plant crop located in the vicinity of a soil moisture sensor and the use of the measurement of soil moisture at two or more depths in the soil combined with data representative of evapotranspiration in the vicinity of the soil moisture sensor and data representative of water in soil events and the determination of the day in which stress in the crop has begun by comparing the water uptake of the crop on days of similar evapotranspiration and whether the water take-up is less than a predetermined difference and if the water take-up is less than the predetermined difference indicating that the latest of the days is the day the crop began to enter a stressed condition.

In an aspect there is a method for indicating the onset of water stress in one or more plants located in a soil the roots of which are within the measurement zone of a soil moisture sensor located in the soil, the soil moisture sensor adapted to provide data representative of the total water volume in millimetres of moisture per 100 millimetres of soil at multiple depths of the soil, at multiple times during a 24 hour period over a predetermined number of consecutive 24 hour periods, and data representative of the values of evapotranspiration within each of a maximum of fourteen consecutive 24 hour periods in the vicinity of the one or more plants is available, and a water in soil detector arrangement in the vicinity of the soil moisture sensor making available data representative of the event of a water into soil event within one or more of the consecutive 24 hour periods, the steps of the method comprising:
  a) determining from representative data there was no recorded water into soil event in the prior 24 hour period of a respective one 24 hour period;
  b) determining from representative data whether there are two respective 24 hour periods of the prior seven consecutive 24 hour periods also have evapotranspiration values within a predetermined range;
  c) determining from representative data the rate of soil moisture depletion during the plant moisture uptake period within each respective 24 hour period adjusted for drainage;
  d) determining whether the rate of soil moisture depletion during the plant moisture uptake period within each respective 24 hour period reduces by a pre-determined level compared to the other of the respective 24 hour period; and
  e) indicating the most recent of the respective two 24 hour periods as a period of water stress of the one or more plants.

In an aspect there is a method for indicating the onset of water stress in one or more plants located in a soil, the roots of which are within the measurement zone of a soil moisture sensor located in the soil, the soil moisture sensor adapted to provide data representative of the total water volume in millimetres of moisture per 100 millimetres of soil at multiple depths of the soil, at multiple times during a 24 hour period or at least following transpiration of the crop ceases, over a predetermined number of consecutive 24 hour periods, and data representative of the values of evapotranspiration within each of a maximum of fourteen consecutive 24 hour periods in the vicinity of the one or more plants is available, and a water in soil detector arrangement in the vicinity of the soil moisture sensor making available data representative of the event of a water into soil event within one or more of the consecutive 24 hour periods, wherein the steps comprise;
  step a) comparing representative data to determine two 24 hour periods of the predetermined consecutive 24 hour periods that are not preceded by a 24 hour period in which there was a water into soil event;

step b) determining from the representative data whether the two respective 24 hour periods of the previous step a) also have evapotranspiration values within a predetermined range, wherein step c) for a first of the respective two 24 hour periods of step b):

determine a first rate of change of the consecutive or extrapolated summed values of soil moisture content in mm/100 mm over a period of at least the period midnight to 3 am;

determine a second rate of change of the consecutive or extrapolated summed values of soil moisture content in mm/100 mm over a period of at least the period 9 am to midday;

determine a third rate of change of the consecutive or extrapolated summed values of soil moisture content in mm/100 mm over a period of at least the period midday to 3 pm;

determine a fourth rate of change of the consecutive or extrapolated summed values of soil moisture content in mm/100 mm over a period of at least the period 9 pm to midnight;

determine the plant related rate of change of the consecutive or extrapolated summed values of soil moisture content in mm/100 mm over a period at least 2 hours either side of noon of the respective 24 hour period;

if and only if the second and fourth rates of change are negative determine a first time of day intersection of the first rate of change with the second rate of change and a second time of day intersection of the third related rate of change with fourth rate of change;

if and only if the first time of day and second time of day fall within 3 am and 9 am the first time of day and the second time of day represent respectively the nominal start and end times of the day of water use by the crop being the plant moisture uptake period, wherein step d) for a second of the respective two 24 hour periods of step b):

determine a first rate of change of the consecutive or extrapolated summed values of soil moisture content in mm/100 mm over a period of at least the period midnight to 3 am;

determine a second rate of change of the consecutive or extrapolated summed values of soil moisture content in mm/100 mm over a period of at least the period 9 am to midday;

determine a third rate of change of the consecutive or extrapolated summed values of soil moisture content in mm/100 mm over a period of at least the period midday to 3 pm;

determine a fourth rate of change of the consecutive or extrapolated summed values of soil moisture content in mm/100 mm over a period of at least the period 9 pm to midnight;

determine the plant related rate of change of the consecutive or extrapolated summed values of soil moisture content in mm/100 mm over a period at least 2 hour either side of noon of the respective 24 hour period;

if and only if the second and fourth rates of change are negative determine a first time of day intersection of the first rate of change with the second rate of change and a second time of day intersection of the third related rate of change with fourth rate of change;

if and only if the first time of day and second time of day fall within 3 am and 9 am the first time of day and the second time of day represent respectively the nominal start and end times of the day of water use by the crop being the plant moisture uptake period, wherein step e) determine whether the degree reduction of the plant related water use during the respective plant moisture uptake periods of the respective 24 hour periods exceeds a predetermined degree of change (by way of example only say 30%); and wherein step f) indicate the most recent of the two respective 24 hour periods as a period of plant stress.

In a further aspect there is a method for indicating the onset of water stress in one or more plants located in a soil the roots of which are within the measurement zone of a soil moisture sensor located in the soil, the soil moisture sensor adapted to provide data representative of the total water volume in millimetres of moisture per 100 millimetres of soil at multiple depths of the soil, at multiple times during a 24 hour period over a predetermined number of consecutive 24 hour periods, and data representative of the values of evapotranspiration within each of a maximum of fourteen consecutive 24 hour periods in the vicinity of the one or more plants is available, and a water in soil detector arrangement in the vicinity of the soil moisture sensor making available data representative of the event of a water into soil event within one or more of the consecutive 24 hour periods, wherein the steps comprise;

step a) if and only if there is no detection of a water into soil event proceed to next step;

step b) for a first of the respective 24 hour periods determine a first rate of change of the consecutive or extrapolated summed values of soil moisture content in mm/100 mm over a period of at least the period midnight to 3 am;

determine a second rate of change of the consecutive or extrapolated summed values of soil moisture content in mm/100 mm over a period of at least the period 9 am to midday;

determine a third rate of change of the consecutive or extrapolated summed values of soil moisture content in mm/100 mm over a period of at least the period midday to 3 pm;

determine a fourth rate of change of the consecutive or extrapolated summed values of soil moisture content in mm/100 mm over a period of at least the period 9 pm to midnight;

determine the plant related rate of change of the consecutive or extrapolated summed values of soil moisture content in mm/100 mm over a period at least 2 hours either side of noon of the respective 24 hour period;

if and only if the second and fourth rates of change are negative determine a first time of day intersection of the first rate of change with the second rate of change and a second time of day intersection of the third related rate of change with fourth rate of change;

if and only if the first time of day and second time of day fall within 3 am and 9 am the first time of day and the second time of day represent respectively the nominal start and end times of the day of soil water use by the crop being the plant moisture uptake period, if and only if the soil water use over the total 24 hour day period reduces, otherwise return to step a);

step c) compensate the soil water use by the crop for drainage over the total 24 hour day;

step d) if and only if there is a previous 24 hour period having data representative of the total water volume, data representative of the values of evapotranspiration, and data representative of the event of a water into soil event; then step e) determine if the evapotranspiration value of the previous 24 hour period is within a predetermined range; if not return to step d);

step f) for the previous 24 hour period:

determine a first rate of change of the consecutive or extrapolated summed values of soil moisture content in mm/100 mm over a period of at least the period midnight to 3 am;

determine a second rate of change of the consecutive or extrapolated summed values of soil moisture content in mm/100 mm over a period of at least the period 9 am to midday;

determine a third rate of change of the consecutive or extrapolated summed values of soil moisture content in mm/100 mm over a period of at least the period midday to 3 pm;

determine a fourth rate of change of the consecutive or extrapolated summed values of soil moisture content in mm/100 mm over a period of at least the period 9 pm to midnight;

determine the plant related rate of change of the consecutive or extrapolated summed values of soil moisture content in mm/100 mm over a period at least 2 hours either side of noon of the respective 24 hour period;

if and only if the second and fourth rates of change are negative determine a first time of day intersection of the first rate of change with the second rate of change and a second time of day intersection of the third related rate of change with fourth rate of change;

if and only if the first time of day and second time of day fall within 3 am and 9 am the first time of day and the second time of day represent respectively the nominal start and end times of the day of water use by the crop being the plant moisture uptake period;

wherein step g) if and only if the degree of reduction of the plant related water use during the respective plant moisture uptake periods of the respective 24 hour periods exceeds a predetermined degree of change (only by way of example only say 30%); then step h) indicate the most recent of the two respective 24 hour periods as a period of plant stress, otherwise continue at step a) but compare the 24 hour period previous to the 24 hour period of step f).

In an aspect step c) of compensating the soil water use by the crop for drainage over the total 24 hour day is calculated by determining the total drop in plant related water use outside the total plant moisture uptake period, and divide by the remainder of the 24 hour period of the day not being the total plant moisture uptake period, and then multiply the result of the division by the plant moisture uptake period and subtract the result of the multiplication from the determined reduction of the plant related water use during the respective plant moisture uptake period to determine the compensated plant related water usage.

The system, method and apparatus disclosed in this specification is intended to provide at least an alternative to the systems currently available and in doing so alleviate or minimise the problems and shortcomings associated with existing systems.

The reference to any prior art or ways of providing provenance in this specification is not, and should not be taken as, an acknowledgement of any form of suggestion that such prior art forms part of the common general knowledge.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

It will be appreciated by those skilled in the art that the disclosure described herein is not restricted in its use to the particular application described. Neither is the disclosure restricted in its preferred embodiment with regard to the particular elements and/or features described or depicted herein. It will be appreciated that the scope of the disclosure is not limited to the embodiment or embodiments disclosed, but is capable of numerous rearrangements, modifications, and substitutions without departing from the scope as set forth and defined by the claims.

Some embodiments described herein may be implemented using programmatic elements, often referred to as modules or components, although other names may be used. Such programmatic elements may include a program, a subroutine, a portion of a program, or a software component or a hardware component capable of performing one or more stated tasks or functions. As used herein, a module or component, can exist on a hardware component independently of other modules/components or a module/component can be a shared element or process of other modules/components, programs or machines. A module or component may reside on one machine, such as on a client or on a server, or a module/component may be distributed amongst multiple machines, such as on multiple clients or server machines. Any system described may be implemented in whole or in part on a server, or as part of a network service. Alternatively, a system such as described herein may be implemented on a local computer or terminal, or server in whole or in part. In either case, implementation of system provided for in this application may require use of memory, processors and network resources (including data ports, and signal lines (optical, electrical etc.), unless stated otherwise.

Some embodiments described herein may generally require the use of computers, including processing and memory resources. For example, systems described herein may be implemented on a server or network service. Such servers may connect and be used by users over networks such as the Internet, or by a combination of networks, such as cellular networks and the Internet. Alternatively, one or more embodiments described herein may be implemented locally, in whole or in part, on computing machines such as desktops, cellular phones, personal digital assistances or laptop computers. Thus, memory, processing and network resources may all be used in connection with the establishment, use or performance of any embodiment described herein (including with the performance of any method or with the implementation of any system).

Furthermore, some embodiments described herein may be implemented through the use of instructions that are executable by one or more processors. These instructions may be carried on a computer-readable medium. Machines shown in figures below provide examples of processing resources and computer-readable mediums on which instructions for implementing embodiments of the invention can be carried and/or executed. In particular, the numerous machines shown with embodiments of the invention include processor(s) and various forms of memory for holding data and instructions. Examples of computer-readable mediums include permanent memory storage devices, such as hard drives on personal computers or servers. Other examples of computer storage mediums include portable storage units, such as CD or DVD units, flash memory (such as those carried on many cell phones and personal digital assistants (PDAs), and magnetic memory). Computers, terminals, network enabled devices (e.g. mobile devices such as cell phones) are all examples of machines and devices that utilize processors, memory, and instructions stored on non-transitory computer-readable mediums.

It should be appreciated that the present disclosure can be implemented in numerous ways, including as a process, an apparatus, a system, or a computer readable medium such as a computer readable storage medium or a computer network wherein program instructions are sent over wireless, optical, or electronic communication links. It should be noted that the order of the steps of disclosed processes may be altered within the scope of the disclosure.

Details concerning computers, computer networking, software programming, telecommunications and the like may at times not be specifically illustrated as such were not considered necessary to obtain a complete understanding nor to limit a person skilled in the art in performing the embodiments, are considered present nevertheless as such are considered to be within the skills of persons of ordinary skill in the art.

The prior summary is provided to introduce a selection of concepts in a simplified form that are further described below in the Detailed Description of Embodiments. That summary is not intended to identify key features or essential features of the claimed subject matter, nor is it intended to be used as an aid in determining the scope of the claimed subject matter.

BRIEF DESCRIPTION OF THE FIGURES

FIG. 2B illustrates some of the more commonly referenced states of the water content of soil that a crop can be subject to;

FIG. 7 depicts an example of the data made available relating to ETo from a Bureau of Meteorology (BoM);

FIG. 9 depicts dawn/sunrise and dusk/sunset times as are made available from the BoM;

DETAILED DESCRIPTION OF EMBODIMENTS

Figure 1:
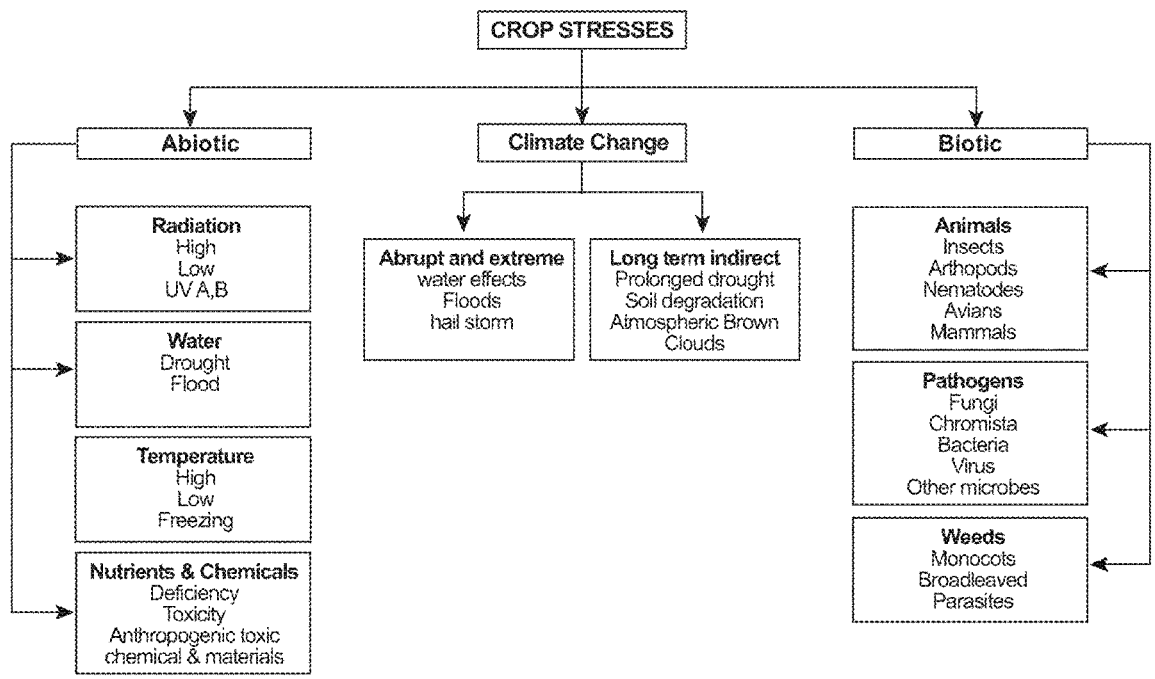
FIG. 1 depicts an overview of biotic, abiotic and climate related factors relating to crop stress.

FIG. 1 depicts a prior art overview of biotic, abiotic and climate related factors relating to crop stress as identified in a paper titled Overview of Plant Stresses: Mechanisms, Adaptions and Research Pursuit M. Maheswari, et al. this list includes many of the causes of stress in plants grouped into related categories and it is clear that any grower will find it impossible to accurately monitor all of them let alone derive any usable information from one or a combination of them. There is sufficient difficulty in understanding some of these categories that academic endeavours to do so are still unclear on the exact mechanism of cause and effect and the degree of change of one characteristics' effect on the plant being in or having experienced stress and the degree of that stress.

The developers of the information disclosed in this specification have taken a different approach to determining water stress in that, in their view the plant itself can provide an indicator of whether it is stressed or has been in a stressed condition. In the view of the developer the best gauge of crop health is daily soil water usage by the crop and the relationship of daily crop water uptake (soil water usage and also referred to herein as daily crop water usage DCWU) compared to when the ETo is similar on separate days. The correct comparison of certain measured values of the soil water usage by the crop being the most revealing characteristic of the health and conversely stressed condition of the plant.

Even in a very dry soil there is a thin film of water held onto soil particles by the force of adhesion and this water is too tightly bound to the soil to be available for plant uptake. Plants however, can access excess water that is held in pore spaces (between soil particles) by osmotic force exerted by the roots of the plant during the day while the process of transpiration takes place enabled by photosynthesis of the above soil portion of the plant. Osmosis is the movement of water molecules from an area of high concentration to an area of lower concentration of water through a partially permeable membrane this can be the cell membrane of the plant. When pore spaces are filled with water, the soil is saturated, and the force of gravity acts on the water to create downward flow though the soil, and thus downward force on the water is ever present no matter the quantity of water within the soil. An additional force on the soil water is that which is exerted by the osmotic force of the roots of the plant. So the soil water is being depleted as the plant and plant roots grow. Infiltration is the process by which water moves into and through a soil. The infiltration rate is governed by the texture and existing moisture. The maximum rate at which the soil can absorb water at a given initial soil moisture content is the infiltration capacity. If rainfall intensity is less than the infiltration capacity, then the infiltration rate will be equal to the rainfall rate. When the rainfall rate is greater than the infiltration capacity, the excess water becomes surface runoff.

Figure 2A:
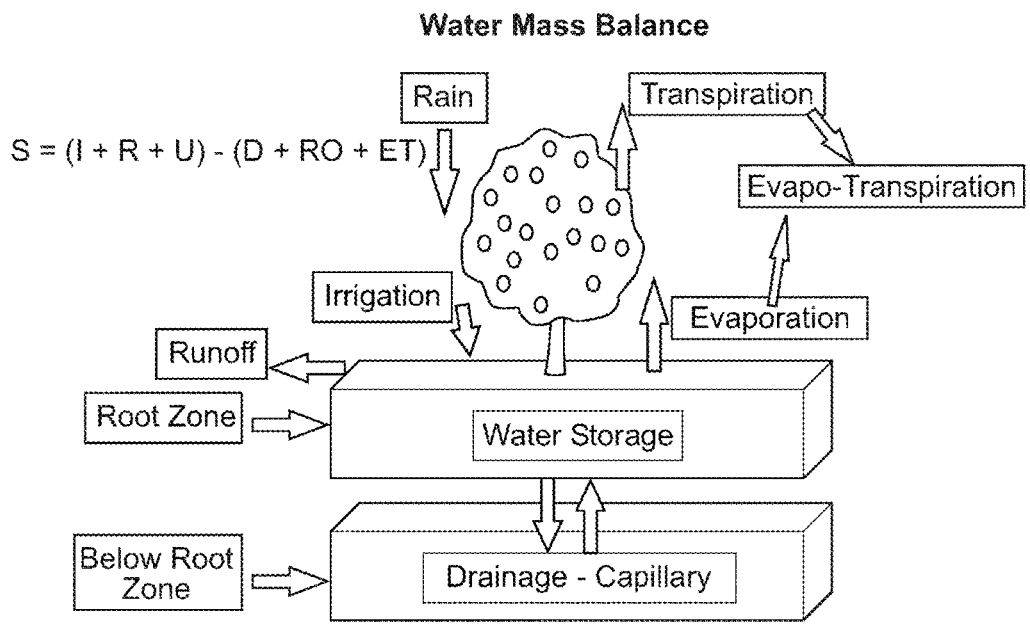
FIG. 2A provides an illustration of the water mass balance in the soil; water; plant; atmosphere continuum.

FIG. 2A provides an illustration of prior known information illustrating the water mass balance in a plant, as well as the above ground environment and the below ground environment. Factors such as those discussed previously, and those that are yet to be described in more detail affect the water uptake of the plant. The simple equation illustrated in FIG. 2A is soil water Storage=(Irrigation+Rain+Uptake)− (Drainage+Run Off+Evapotranspiration).

Figure 2B:
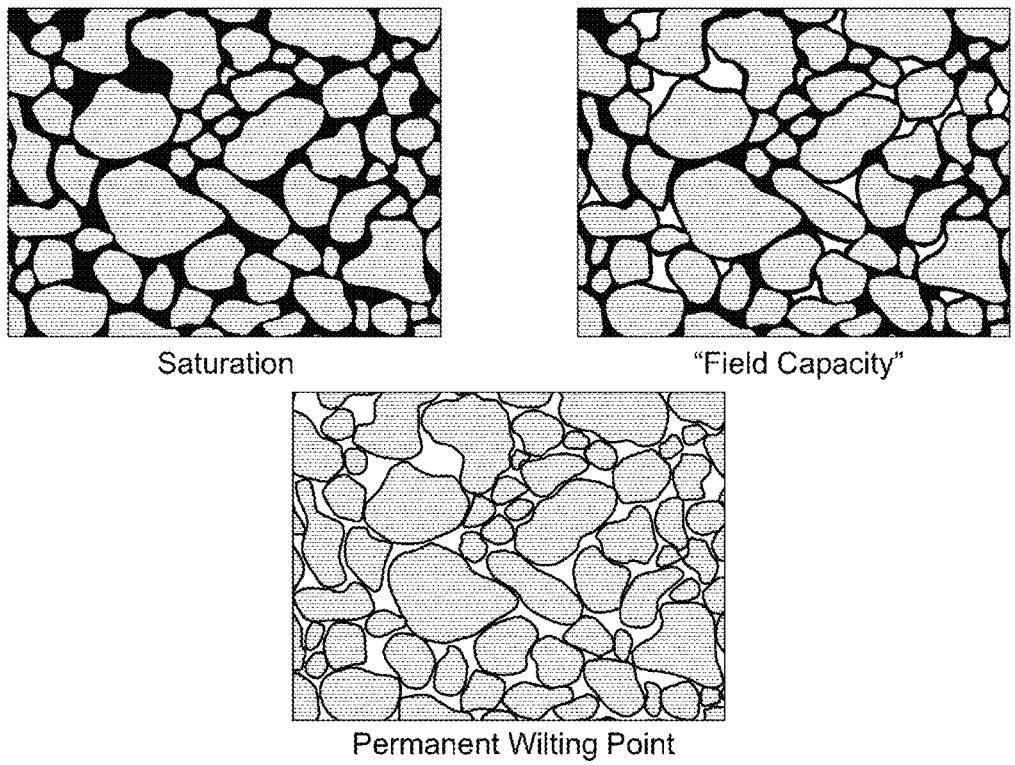

FIG. 2B is illustrative of some of those features described above and illustrates some common terms used in the description.

Figure 2C:
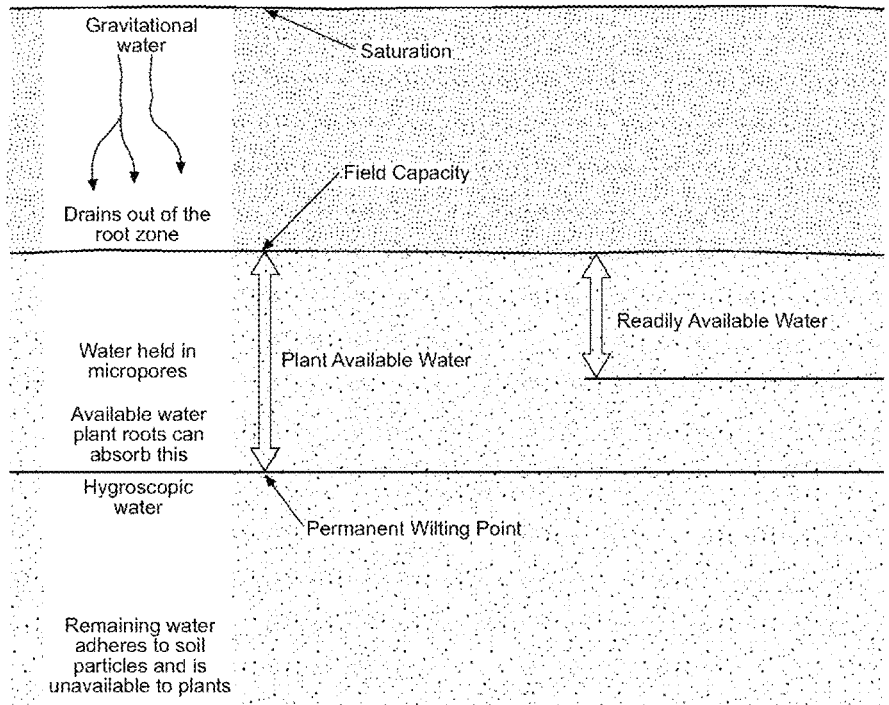
FIG. 2C is another illustration of the concept of the difference between plant available water and readily available water.

FIG. 2C illustrates some of the more commonly referenced states of the water content of soil which support a crop and illustrates some common terms used in the description.

Water saturation is a condition of soil that is reached when all easily drained voids (pores) between soil particles are temporarily or sustainably filled with water. This condition can be reached during the water into soil event and can remain in that state for a period of time depending on the drainage characteristics of the soil, soil water evaporation and plant water uptake.

Soil water potential describes how tightly the water is held in the soil. Soil water tension (or suction) is another term used to describe soil water potential. It is an indicator of how hard a plant must work to get water from the soil. The drier the soil, the greater the soil water potential and the harder it is to extract water from the soil. To convert from soil water content to soil water potential requires information on soil water versus soil tension that is available for many soils.

Water in the soil can be classed as plant available or plant unavailable water. FIG. 2B also illustrates other major states of soil water in a soil supporting a crop—Field Capacity and Permanent Wilting Point these terms being defined below.

Field capacity is the point at which the gravitational or easily drained water has drained from the soil. Traditionally, it has been deemed in the USA as ⅓ bar tension. However, field capacity in Australia for many irrigated soils is deemed to be approximately ⅒ bar tension being indicative of the maximum amount of water which can be held against gravity.

Permanent Wilting Point is the soil moisture content where most plants would experience permanent wilting and is considered to occur at 15 bars tension.

As illustrated in FIG. 2C, Plant Available Water (PAW) is defined as the water held in the soil between field capacity and wilting point.

Readily Available Water (RAW) is that portion of the available water that is relatively easy for a plant to use without experiencing water stress (this is determined by the plant condition). Even though all of the available water can be used by the plant, the closer the soil is to the wilting point, the harder it is for the plant to use the water. Plant stress and yield loss are possible after the readily available water has been depleted even though there may still be water in the soil.

Figure 2D:
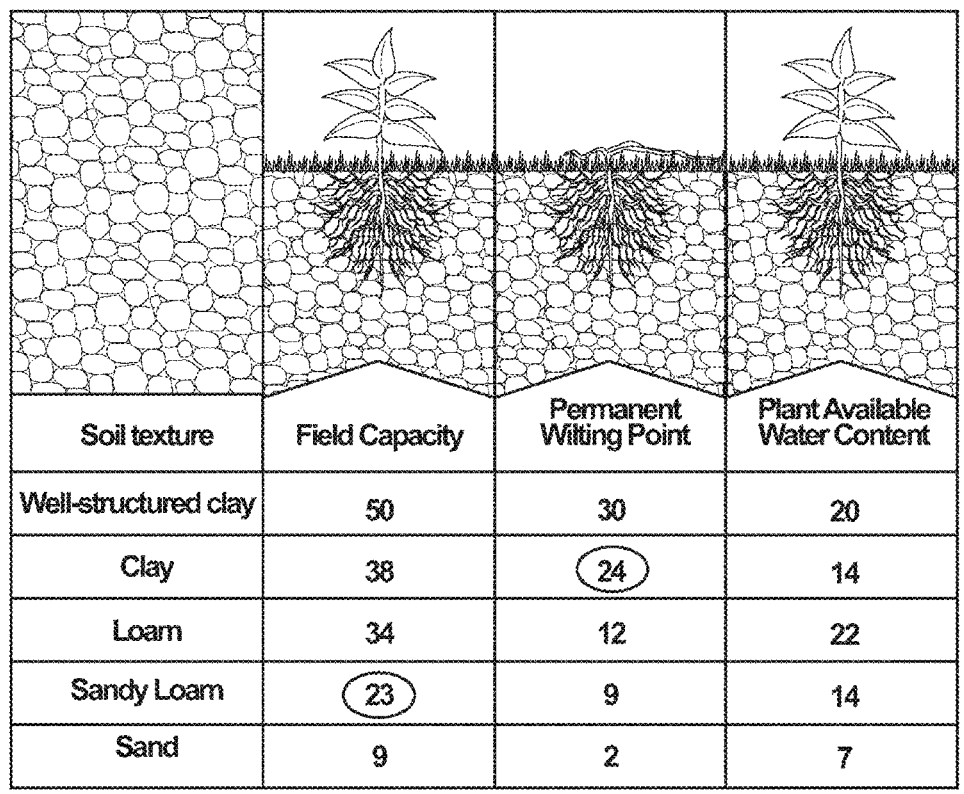
FIG. 2D illustrates that the texture of the soil also has an influence on the Field Capacity, Permanent Wilting Point, and Plant Available Water Content.

FIG. 2D illustrates that the texture of the soil also has an influence on the Field Capacity, Permanent Wilting Point, and Plant Available Water, illustrated best by noting the very different values of cm of water in 1 meter depth of the respective soil (this being a different measure than described below but used to create this particular illustration). Whereas well-structured clay has a field capacity of 50 cm, sand has a field capacity of 9 cm (most water will drain away), contrasting those same soil types having 20 cm and 7 cm respectively of plant available water and permanent wilting points of 30 cm and 2 cm (indicating that the lower suction forces required to extract water from sand). Very simply, the illustration is also illustrative of the Field Capacity being the total of the Plant Available Water Content plus the Permanent Wilting Point, e.g. for clay 38 cm=14 cm+24 cm in a meter of that soil type. Noting of course that there is still a difference between the amount of water representing the permanent wilting point and the readily available water (FIG. 2C).

Of course there are many different methods for determining the water up take of a plant including: direct destructive testing of the plant or portions of the plant; analysis of the spectral radiation from the plant which detects a variety of characteristics not only water content; soil moisture content of the soil in the vicinity of the root zone of the plant is an indirect measure of the uptake characteristic and there are many methods of making a measurement of the soil moisture content including the following techniques.

Gravimetric or volumetric measurement requiring the removal and destruction of soil samples to determine soil moisture content. This method is not practical for continuous measurements and since it is destructive it can only be used once or otherwise take time, as the measurements can only be conducted remote of the sample location.

In situ reflectometer which uses time domain reflectometry (TDR) wherein determinations involve measuring the propagation of electromagnetic (EM) waves or signals, wherein propagation constants for EM waves in soil, such as velocity and attenuation, depend on soil properties, especially water content and electrical conductivity. The dielectric constant, measured by TDR, provides a measurement of soil water content and is essentially independent of soil texture, temperature, and salinity and the measured parameter is volumetric water content. Since the measurement utilises the propagation of a series of controlled electromagnetic waves and the detection of reflections from the soil moisture within the sampling zone there is a response time of approximately 30 seconds per measurement but it is possible to perform long term in situ measurements which can be automated so that soil moisture data is made available over time at required intervals.

Resistive soil moisture measurement involves the insertion of two electrically conductive probes into the soil and the passage of a current or currents from one probe to the other and the measurement of the effective resistance of the soil which is indicative of the conductivity of the soil and in theory the higher the moisture content the higher the conductivity (the relationship also being the lower the resistance the higher the conductivity) and the use of soil type characteristics to look up the moisture content, all of which can be automated once there has been a calibration process undertaken.

Capacitive soil moisture measurement sensors can be used to determine soil moisture, which for the purposes of an example of the method of plant stress determination disclosed in this specification, a buried array of capacitive soil moisture sensors. The use by way of example in this specification of capacitive soil moisture sensors is in no way meant to indicate that there are no other soil moisture determination techniques that could be used. Yet further, a particular configuration of multiple of such sensors is used in the figures associated with this description, since they are known to the developer of the methods disclosed herein, in particular, the arrangement of sensors disclosed in the patents incorporated in full by reference into this specification and all commonly owned by the owner of the development disclosed herein.

Figure 3:
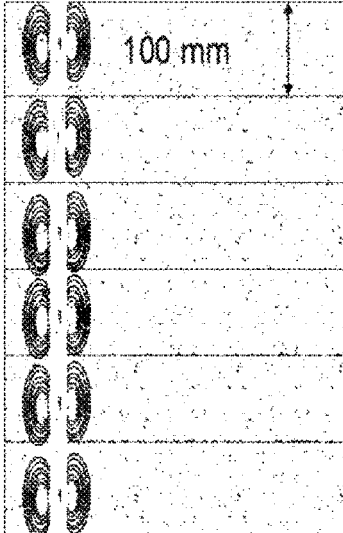
FIG. 3 depicts a soil water content determination involving multiple soil moisture sensors located in soil at predetermined depths in linear array and an illustration of the total water content determination.

Multiple sensors in a vertical array (whatever type the sensor may be) and their output values are usable to determine at predetermined intervals over each 24 hour period (typically a day midnight to midnight) the total soil moisture value in the vicinity of the sensor array which is in the vicinity of the crop plants in particular the root zone of the crop. The use of an array of sensors, typically a linear array (vertically disposed in a close fitting aperture in the soil) is arranged to detect soil moisture at locations within the soil and in particular, to a depth along and to at least below the depth of the root zone of the respective plant or at least for the whole of the plant growth period which may require the depth of the sensor array to be well below the starting depth of the root but deep enough to not have the roots grow below the lowest zone from which the soil moisture field of influence can measure soil moisture values. FIG. 3 is illustrative of such an array and more will be described about the array later in the specification.

The definitions provided are to assist the reader but should not be presumed to limit the scope of the claims.

Soil water content most commonly is expressed as percent water by weight, percent water by volume, or mm of water per 100 mm of soil or inches of water per foot. Example: 12 mm of water per 100 mm of soil (this can also be expressed as 12% water content) or 0.472441 inches of water in 3.93701 inches of soil or 1.417323 inches of water per foot of soil.

Water content by volume is obtained by multiplying the water content by weight the bulk density of the soil. Bulk density of the soil is the relative weight of the dry soil to the weight of an equal volume of water. Bulk density for typical soils usually varies between 1.25 and 1.8.

Inches of water per foot of soil is obtained by multiplying the water content by volume by 12 inches per foot. It also can be expressed as inches of water per inch of soil which is equivalent to the water content by volume. By determining this value for each layer of soil, the total water in the soil profile can be estimated by adding up each consecutive measurement. There is also a metric measure being mm of soil water/100 mm of soil. This is illustrated in FIG. 3 for a metric measurement using capacitive soil moisture sensors (to be described in greater detail later in the specification).

Figure 3A:
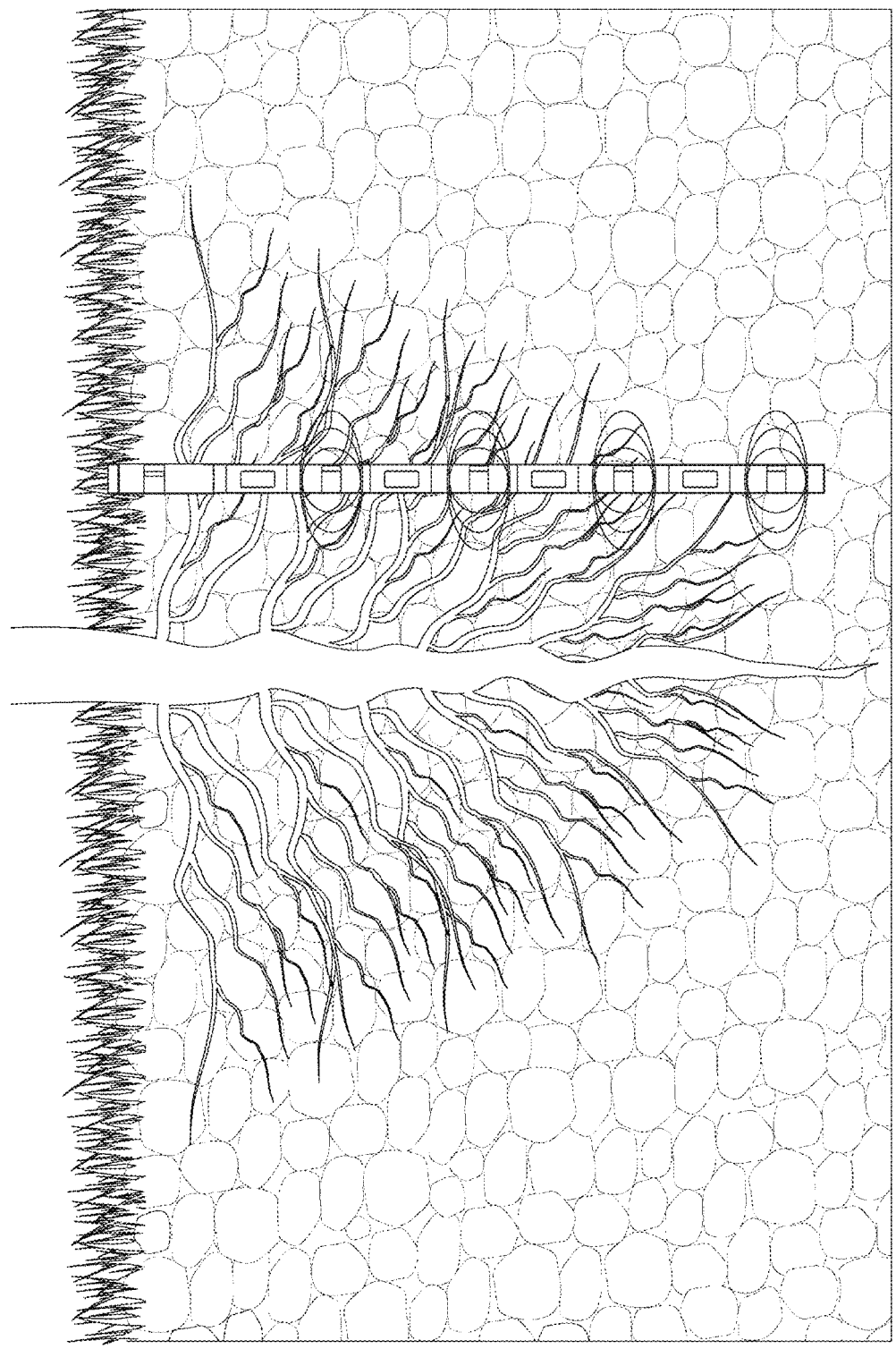
FIG. 3A is illustrative of the location of an array of soil moisture sensors in the root zone of a plant.

FIG. 3 depicts a soil water content determination involving multiple soil moisture sensors located in soil at predetermined depths in a linear array and an illustration of the total water content determination created by adding the measured soil moisture content at each depth of measurement, e.g. 12 mm (@10 cm)+10 mm (@20 cm)+15 mm (@30 cm)+21 mm (@40 cm)+25 (@50 cm)+28 mm (@60 cm) to be summed to the value of 111 mm. Of note is that since the sensors are spaced 10 cm apart the effective volume of soil measured is 100 mm so the total water content is in the recognised measurement scale of mms/100 mm. Other arrangements are possible and the measurement and representation of the total soil moisture content can be readily derived. It will also be noted that the soil moisture content measured by each sensor is at a particular time of the day and so as to represent the total soil moisture content at that time of day, all the sensors conduct their measurement at effectively the same time. It need not be absolutely coincident understanding that the movement of water within the soil is a long term process compared with the very short measurement period of seconds. FIG. 3A is illustrative of the location of an array of soil moisture sensors in the root zone of a plant, with the lowest sensor located at the depth of the expected depth of the deepest roots.

For the purposes of the embodiment described herein the total soil moisture content for a region in the vicinity of the plants to be determined as being at or having been under stress is calculated in this embodiment, by summing, as indicted above, all the soil moisture values for each of the individual sensors in the array of sensors. Thus, if there were only 3 such sensors with the same spacing of about 10 cm, the root system of the plant would not be expected to be much deeper than 40 mm into the soil if the output values are to be expressed in the recognised measurement scale. However, adjustment could be made to the calculation of the total soil moisture values when less or more sensors are arrayed to achieve a figure using the recognised measurement scale. For example, the sensors may have a field of influence which is larger or smaller than the 100 mm in which case the volumetric calculation is accordingly adjusted, this being a mathematical adjustment.

Figure 4:
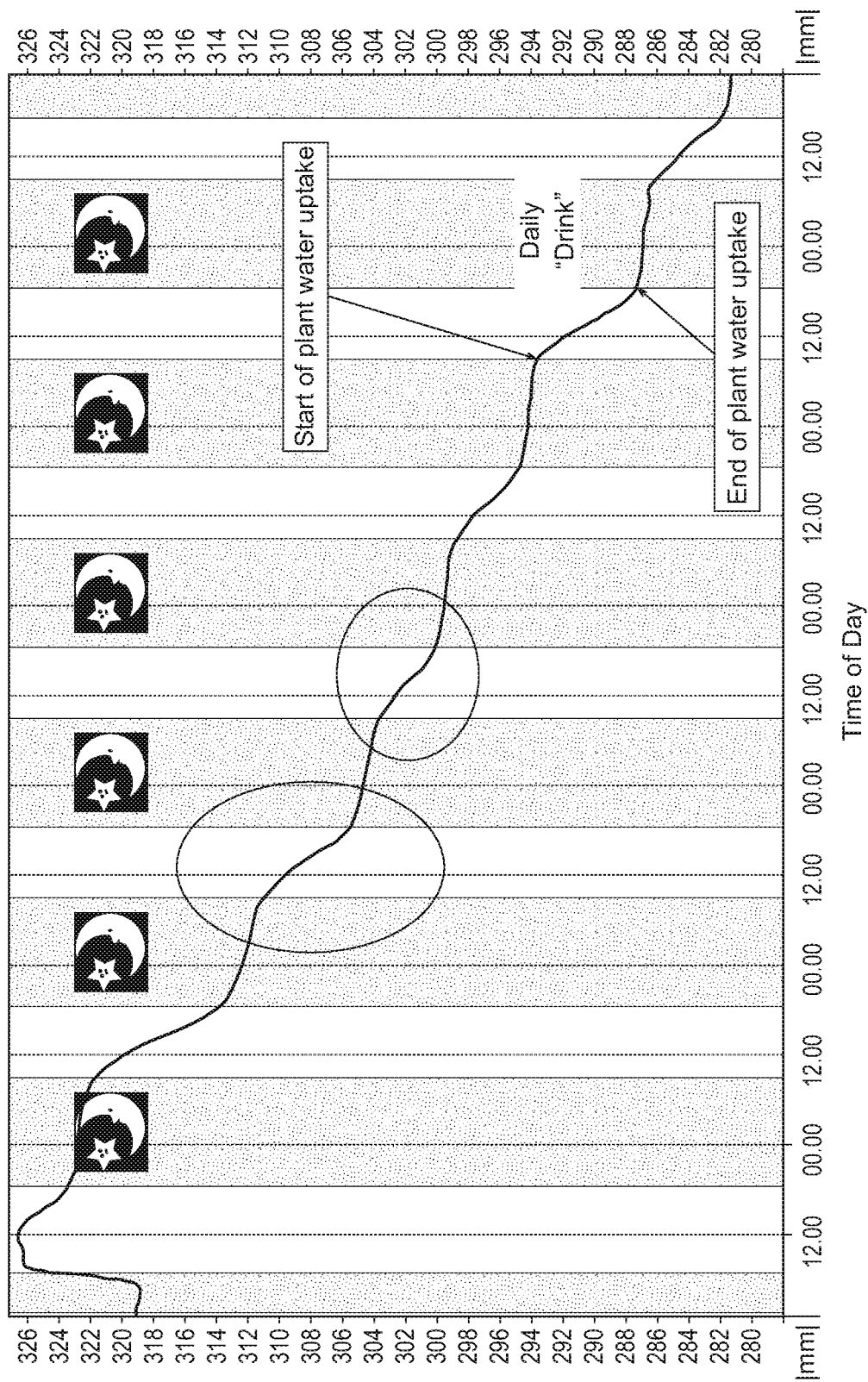
FIG. 4 depicts the plotted total water content values of soil moisture from an array of sensors which extend from the soil surface to at least below the root zone of the plants in the vicinity of the sensor array over 7 consecutive days.

FIG. 4 depicts the plotted values of soil moisture as a sum from an array of sensors which extend from the soil surface to at least below the root zone of the plants in the vicinity of the sensor array. Seven consecutive 24 hour periods (7 days) of measurements are displayed as depicted along the horizontal axis and the summed soil moisture content is provided along the vertical axis showing a maximum of 328 mm and a minimum of 280 mm. The grey vertical columns are illustrative of the night period and the intermediate white columns are daylight hours.

The continuous line which begins at a 319 mm value during the night of day 1 illustrates the summed soil moisture values, which is the sum of all the values taken from all the individual sensors of the sensor array at 10 minute intervals for the total measurement period. The interval between measurements is a decision which is made based on a number of factors, the most important one being the capacity of the measurement and recordal system to collect and store (locally or remotely) the data generated, knowing that the smaller the interval between measurements the more data to be handled by the system. An advantage of a small interval is that the granularity of the measurements allows for close examination of the actual time of the changes that occur to the soil moisture values. There are steps in the embodiment method described later which may or may not provide more accurate output information dependant on the quantity of data to perform the step/s on and ten minutes may not be the actual measurement interval used.

The continuous line within the morning to night portion of day 1 rises sharply upwards, which is indicative of a water into soil event (e.g. rain or planned watering of the crop) the soil moisture level rising to the level of about 326 mm and after midday (1200 hours) beginning to reduce such that by the onset of dusk the soil moisture has fallen to about 322 mm. As will be observed in the data provided in this chart, the soil moisture level remains much the same, or drops very little during the night period. The drop in soil moisture level being largely attributable to water draining below the effective measurement zone of the array of sensors, since there is no transpiration of water out of the plants during the night, and none or very minimal evaporation of water from the soil.

As dawn passes and daylight time of day 2 begins, transpiration also begins indicated by the lowering of the soil moisture value from a starting level of about 322 mm to 314 mm by the end of daylight and the onset of dusk.

The night period of day 2 into day 3 shows a similar lack of lowered soil moisture level to that of the night of day 1 in that the level drops from about 312 mm to 305 mm. While the drop in soil moisture level during day 2 3 is 310 mm to 305 mm, this being a larger drop during the daylight hours than for day 2. This could be attributed to a growth spurt by the plants or as will become more apparent later, due also to atmospheric conditions, such as for example, hot winds, air temperature and solar radiation, which increase the transpiration of water from the root system to the plant leaves and into atmosphere as transpiration from the plant and evaporation from the surface of the soil (ETo), total Evapotranspiration.

The night period of day 3, like other night periods is shown to have a minimal effect on the soil moisture levels in the vicinity of the plants since the drop in soil moisture level is 305 mm to 303 mm.

Day 4 soil moisture level decreases indicative of (ETo) levels, which indicate that the soil moisture levels reduced from 303 mm to about 300 mm, the uptake of water being less than during day 3, which could be again due to atmospheric conditions (ETo) since some days there would be little growth of the crop. The night period of day 4 is again much like prior nights as indicated by a fall in soil moisture levels from 300 mm to a level of about 299 mm.

Day 5 soil moisture level decreases indicative of transpiration levels which indicate that the soil moisture levels reduced from 299 mm to about 295 mm, the uptake of water being slightly more than during day 4, which could be again due to growth factors, and atmospheric conditions (ETo). The night period of day 5 is again much like prior nights as indicated by a similar fall in soil moisture levels from 295 mm to a level of about 293 mm.

As indicated and most likely clear from the descriptions thus far, the plant transpiration period of day 6 begins at dawn each day (depicted in words in FIG. 4 as the START OF PLANT WATER UPTAKE) and the day light period being the DAILY DRINK of the plants and the dusk time being the END OF PLANT WATER UPTAKE. Day 6 soil moisture level decreases indicative of transpiration levels indicate that the soil moisture levels reduced from 293 mm to about 287 mm. The night period of day 6 is again much like prior nights as indicated by a fall in soil moisture levels from 287 mm to a level of about 286 mm.

Day 7 soil moisture level decreases due to transpiration levels indicate that the soil moisture levels reduced from 286 mm to about 282 mm, the uptake of water being slightly more than during day 4, which could be again due to growth factors and atmospheric conditions (ETo).

Figure 5:
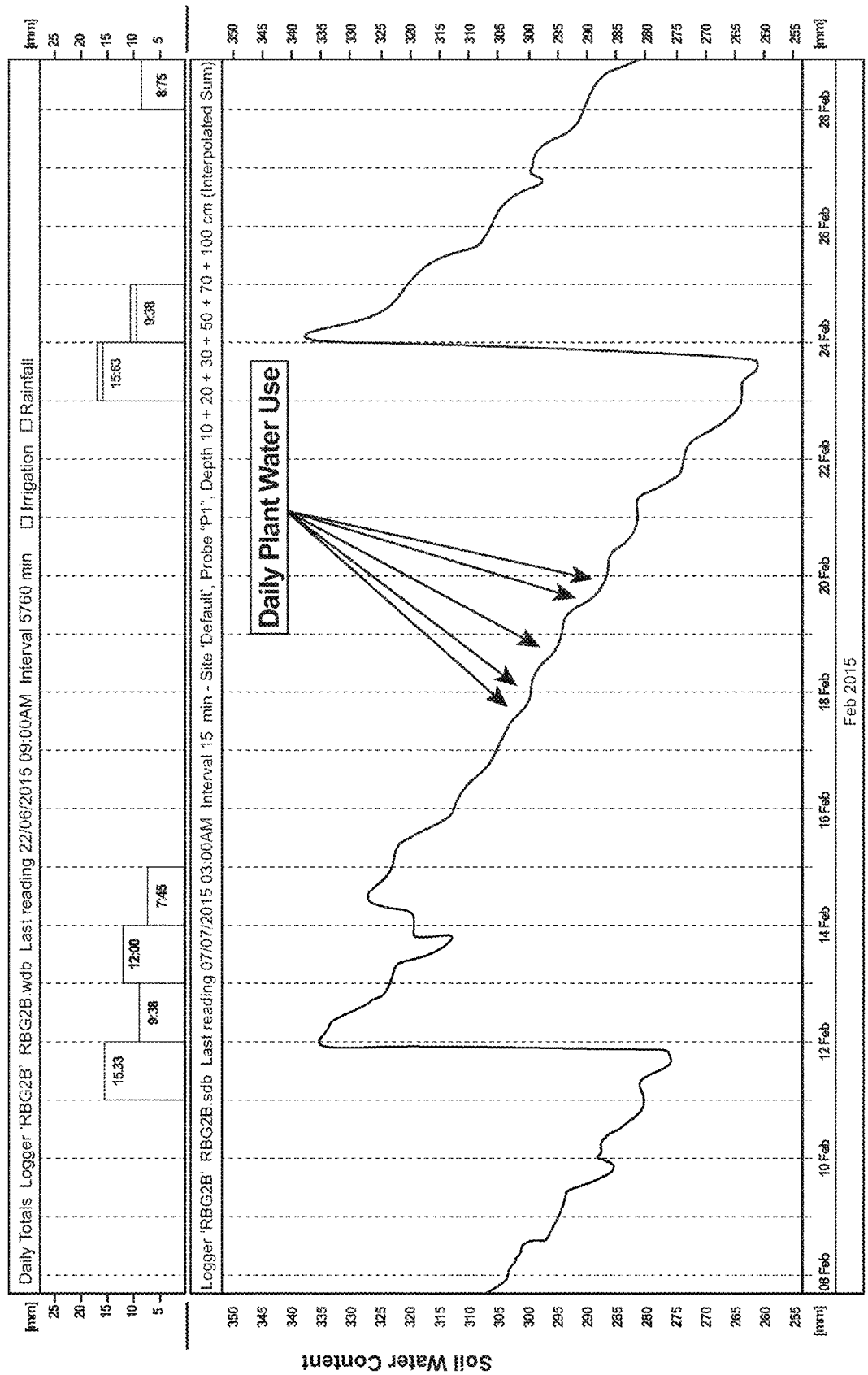
FIG. 5 depicts the near continuous plotted total water content values of soil moisture from an array of sensors which extend from the soil surface to at least below the root zone of the plants in the vicinity of the sensor array over 11 consecutive days.

FIG. 5 depicts the plotted values of soil moisture from an array of sensors which extend from the soil surface to at least below the root zone of the plants in the vicinity of the sensor array over 11 consecutive days. The trace depicts the occurrence of a major water into soil event (e.g. rain or planned watering of the crop) the soil moisture level rising on the 12th of February and also on the 24 February, and a smaller water into soil event on the 14th of February. The most obvious feature of the trace, by now, is the staircase pattern of the line over consecutive days, indicative of the continuous lowering of the soil moisture level. The upper band of the chart depicted in FIG. 5 illustrates the measured water into soil events being rain and irrigation and their respective levels as measured in the field over respective 24 hour periods. As depicted in respect to the 23rd and 24th of February two types of water into soil events occurred.

Reference is made to ETo levels and those values are obtainable in a number of measured ways, and also capable of being obtained from a number of different sources. For example, Bureaus of Meteorology (BOM) are tasked with, amongst many other duties, to provide ETo levels for many regions within their area of responsibility. See also the information relating to FIG. 7.

Figure 6:
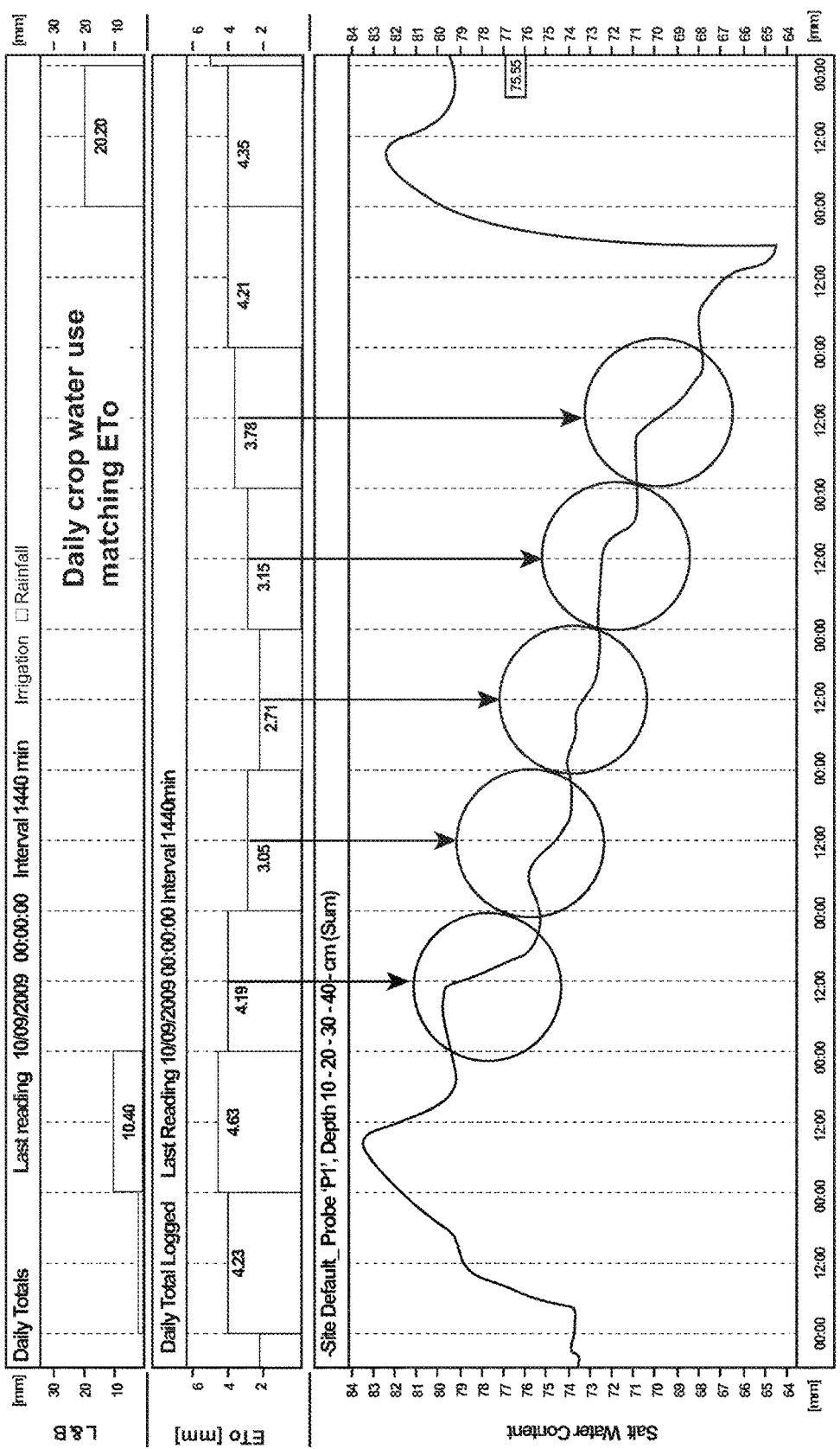
FIG. 6 depicts a further plot of total water content values over many consecutive days, the level and day of water into soil events, and the Evapotranspiration (ETo) levels for each day.

FIG. 6 depicts an example of soil water depletion or crop water use during day light hours subjected to the prevailing ETo of that day. The graphical representation of the collective soil moisture values of an array of soil moisture sensors located in the soil in the vicinity of the crop, showing declining ETo relates to a declining daily step in water use (refer in FIG. 6 to the 3 downward arrows starting from the left-hand side of the figure) and an increasing ETo indicative of an increase in the daily water use indicated by the steepness of the water use step (refer in FIG. 6 to the last 2 arrows on the right-hand side of the figure). This relationship of a concordance of the increase and decrease of crop water use and ETo is evident when the crop is not under water stress.

A numerical example for a non-stress scenario not related to the graph is provided as follows for illustrative purposes only.

Day 1: ETo is 10 mm, crop water use is 6 mm, Day 2: ETo is 8 mm, crop water use is 4 mm. Day 3: ETo is again 10 mm and crop water use is back to 6 mm.

Under the same ETo conditions experienced within say the last 4-5 days, the crop should show the same water use as the water take-up by all means, including the growth of the surrounding crop should be much the same within a couple of days. However, the graphical representation of the water take-up does not illustrate that. The developer has identified that the crop is likely in a water-stress condition. The crop is considered to be in a condition that cannot transpire at the same rate as previously was the case, since the remaining soil water is bound too tightly to the soil particles. Soil water removal rate diminishes causing a slow-down in transpiration rate.

A numerical example for a crop stress scenario not related to the graph of FIG. 6 is provided as follows for illustrative purposes only.

Day 4: ETo is 10 mm, crop water use is 6 mm, Day 5: ETo remains at 10 mm, but crop water use now dropped to 5 mm (it should have been 6 mm), Day 6: ETo still at 10 mm, but crop water used dropped further to 4 mm, Day 7: ETo dropped a little, crop water use now at 2 mm (note: on an ETo day of 8 mm it should have been 4 mm and not 2 mm, refer to the numerical example noted above).

So the developer has determined that the detection of the onset of water stress can be achieved by comparing a number of ETo days and the corresponding crop water use for those days, as long as the days of comparison follow an irrigation and rainfall event and are not interrupted by an irrigation or rainfall event as in one embodiment determined by a water in soil detector arrangement. Onset includes the principle that a preceding day that meets the conditions identified by the developer is an indicator of stress and that if those conditions continue then further stress will ensue, hence the term onset.

The pairs of ETo and crop water use figures for each day can be recorded in mm: ETo mm and crop water use mm on a particular day. Although the comparison is done following a daily measurement and is thus a lagging indicator, the collection and comparison process can be commenced immediately the end of the daily water take-up measurement is calculated, which is effectively as soon as night falls, since transpiration also ceases at that moment.

The day when the pairing of ETo and Crop Water use water use drops below a previously recorded pairing when the ETo associated crop water use is lower than previously recorded under the same or higher ETo conditions, is the first day that water stress is indicated by this analysis.

FIG. 7 depicts an example of the data made available relating to ETo from a BoM for a particular day (24 hour period midnight to midnight), including in this example, a figure representing the ETo expressed in mm of moisture within a range of zero to 2400; the rain fall for that day in mm; Pan evaporation being a measurement that combines or integrates the effects of several climate elements: temperature, humidity, rain fall, drought dispersion, solar radiation, and wind; maximum and minimum temperature on degrees centigrade; maximum and minimum relative humidity being the amount of water vapour present in air expressed as a percentage of the amount needed for saturation at the same temperature expressed as a percentage (%); average 10 m above ground wind speed in meters per second; and solar radiation expressed in mega joules per square meter. The ETo values apply to an area of the geography which could for example cover multiple cropped areas in that vicinity. There is no reason that the ETo value used apply to the very exact region of the crop which is being monitored by way of in one example, soil moisture recordal, etc. so an ETo value for the region will suffice. By way of illustration using the data provided in FIG. 7, the distance between Kent Town and the Adelaide Airport is approximately 10 kms and the ETo values are respectively 5.9 mm and 5.4 mm; the distance between Kent Town and Clare High School is approximately 145 kms and ETo values are respectively 5.9 mm and 6.2 mm; and the distance between Kent Town and Coober Pedy Airport is approximately 900 kms and ETo values are respectively 5.9 mm and 9.4 mm.

Referring back to FIG. 6 there are five circled regions of the soil moisture curve highlighting the soil moisture reduction during daylight hours of five consecutive days, and arrows from the respective ETo value for those days. It is noted that there appears to be a rough correlation between the slope of the daily reduction of soil moisture levels with the corresponding level of ETo, wherein the higher the ETo level the greater the slope thus indicating the greater transpiration of the crop hence the greater take up of moisture from the soil and when the ETo is lower the slope is less, comparatively, indicating the lesser transpiration of the crop hence the lower take up of moisture from the soil.

It will be recognised that although ETo is a daily figure the actual effect on the plants is likely to be greater during the daylight hours but there can still be effects during the night. Again for the embodiment described herein the daily level of ETo suffices for the purposes at hand.

This document provides disclosure of at least one method for determining that a crop is entering a stress condition or has recently suffered a stress condition.

Figure 8:
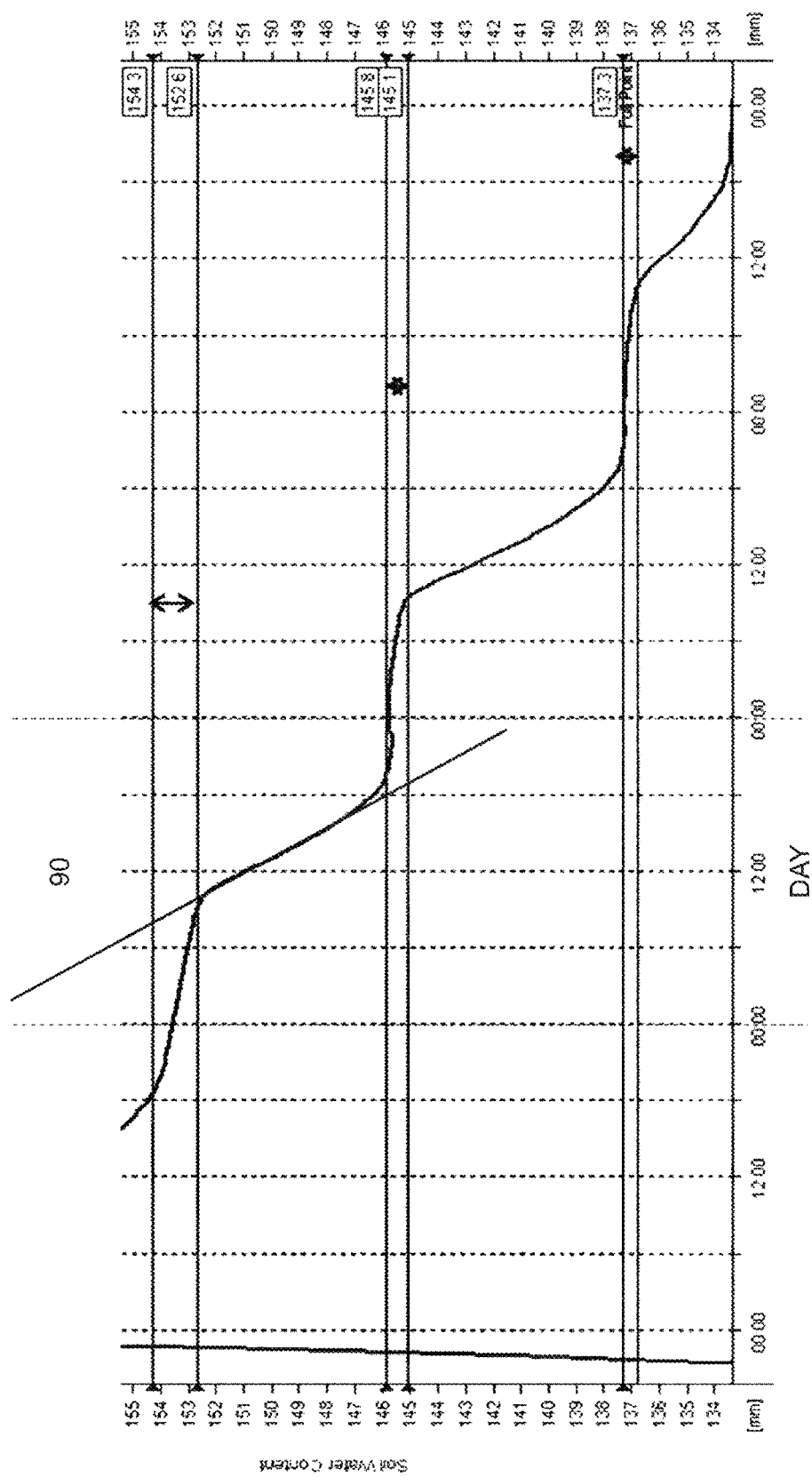
FIG. 8 depicts a single daily soil water measurement cycle for a plant crop as determined by a single array of multiple soil moisture sensors located in the vicinity of the plant crop.

In an aspect the method is exemplified by the following processes and as illustrated by the graphical representation in FIGS. 8 and 9 and others.

FIG. 8 depicts a highlighted single daily soil water measurement cycle for a plant crop as determined by a single array of multiple soil moisture sensors.

The continuous staircase shaped total soil moisture uptake curve is of particular interest within the 24 hour period denoted DAY being from midnight to midnight of that DAY. The curve is observed to follow an almost linear path during a period of the day which coincides with the daylight hours and indicates that the plant crop is taking up soil moisture (transpiration) at an almost constant rate, although it is recognised that a portion of the decrease in total soil moisture is due to natural draining of the available soil moisture due to gravitational force on the soil water. The value of total soil moisture at the beginning of the almost linear portion is determined as being at the intersection of the linear path 90 with the horizontal line indicating a value of soil moisture of 152.6 mm at a time 10 am. While the end of the almost linear portion is determined as being at the intersection of the linear path 90 with the horizontal line indicating a value of soil moisture of 145.8 mm at a time of 6 pm. The calculation of a slope is simply (152.6 mm-145.8 mm)/8 hours=0.85 mm/hour.

Although the graphical representation provides a simple means to observe the various values the data used to create the graph can equally be used by a processor, suitable program and memory to produce the same outcome, being a determination of the rate of soil water uptake of the plant crop in the vicinity of the soil moisture sensor array. The method for determining the linear path is less obvious but there are methods known, when requested to conduct such an analysis, to those of skill in the art to determine from the raw total soil moisture values and the times they were recorded. They may apply, for example, a least squares analysis to the data, to determine a line of best fit for collection of data that exist between groupings of data having, for example, variously and comparatively, large and small differences between successive times of recordal, or alternatively the daylight start and end time, for the region in which the soil moisture sensor array is located can be used to approximate the times within the data collected, to begin the least square analysis. Indeed, dawn/sunrise and dusk/sunset times are available from the BoM as depicted in FIG. 9.

Therefore, in respect of any soil moisture data previously recorded, it is possible to apply additional information even if it was not collected at the time and apply the methods disclosed herein to determine slopes indicative of soil moisture up take for plant crops and determine one or more characteristics about the plant crop growth.

Figure 10:
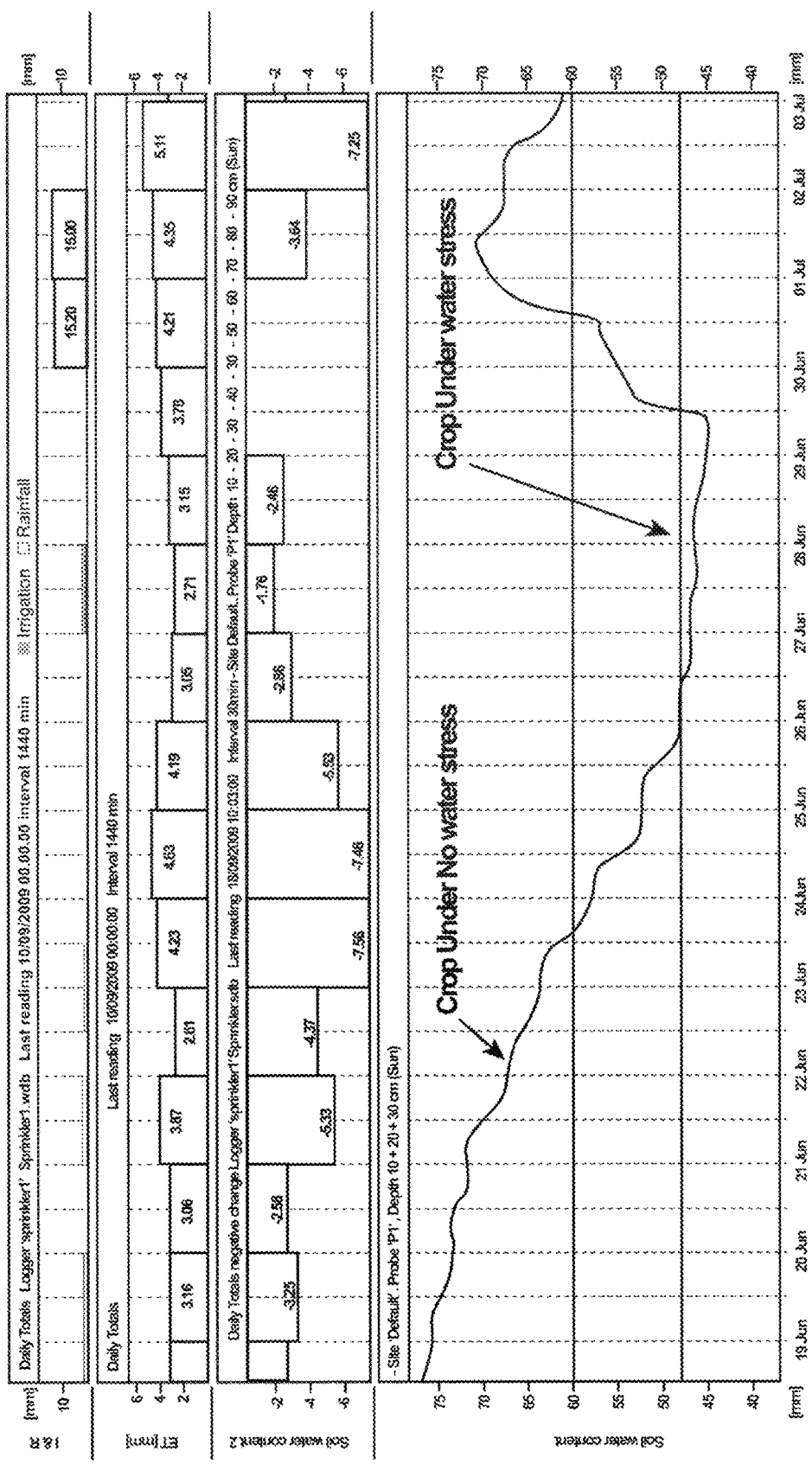
FIG. 10 depicts an array of four charts indicating water in soil event, daily ETo values, total soil water usage, and soil water content in the vicinity of a plant crop over a 15 day period.

FIG. 10 depicts an array of four charts of water in soil event, daily ETo values, total soil water up take, and soil water content in the vicinity of a plant crop over a 15 day period. The graphs are representative of the available data some of which is collected from sources such as the BoM, and other data as provided by a soil moisture sensor array, which in this example is a 7 sensor array collecting soil moisture readings from depths of 10 cm, 20 cm, 30 cm, 40 cm, 50 cm, 70 cm and 90 cm and summed from all the sensors of the measured soil moisture is made available over extended period of 18 June to 3 July, the dates being figurative only. The $22^{nd}$ and $27^{th}$ of June have very similar ETo values, but the Daily Crop Water Use is quite different.

Two 24 hour periods for 23 June and 28 June are indicated by the two rectangular boxes and in the lower chart, one box is titled "Crop under no stress", and the other box is titled "Crop under stress". These determinations are made based on an analysis of at least the ETo, the total moisture uptake during the relevant 24 hour period, and most relevantly the same data for prior 24 hour periods. Hence, with respect to the earlier 23 June, it is apparent that all the prior 24 hour periods display a typical staircase shape of the soil water uptake where the ETo changes 3.16, 3.05, 3.87 and finally on 23 June the ETo is 2.26 as does the total soil moisture uptake being respectively 3.25 mm, 2.58 mm, 5.33 mm and finally on 23 June 4.37, whereas the period beginning 24 June starts out exhibiting the typical staircase shaped soil water uptake where the ETo values are 4.23, 4.63, 4.19, 3.05 and then 2.71 on 28 June which is not that much more variable than the days 19 June to 23 June, but the total soil moisture uptake begins on 24 June as 7.58 mm, 7.46 mm, 5.53 mm, 2.86 mm and then on 28 June 1.76 mm. During the period 19 June to 23 June there were two small (about 1 mm) rain falls (water in soil events), and during the period 24 June to 28 June there was a similar rain fall event on 24 June and an irrigation event of 28 June.

Figure 11A:
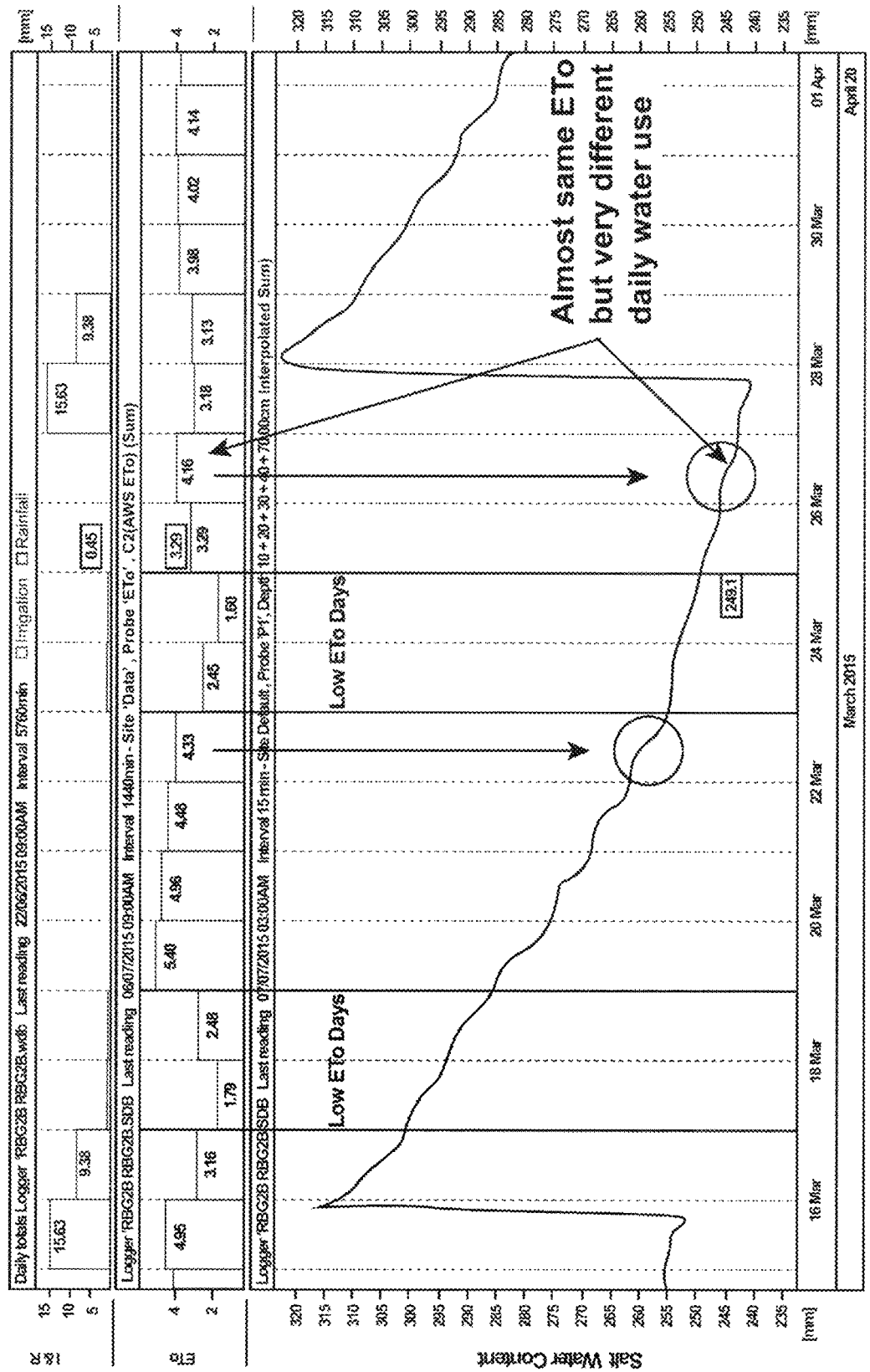
FIG. 11A depicts two successive low ETo days and the occurrence of two different days with similar ETo days but very different daily soil water usage.

FIG. 11A is Illustrative of the crop reaction to water availability, where after two successive low ETo days there can be similar ETo days (namely 4.33 and 4.16 values) as are the case at the location of the days highlighted by downward arrows and red circles about the referenced daily water usage (DWU), but very different daily water usage, as indicated by the substantially lower slope of the sunlight periods of 22 March and 26 March respectively. As identified in this disclosure the lower DWU of 26 March is due to the difficulty the crop has in extracting the water from the soil.

Figure 11B:
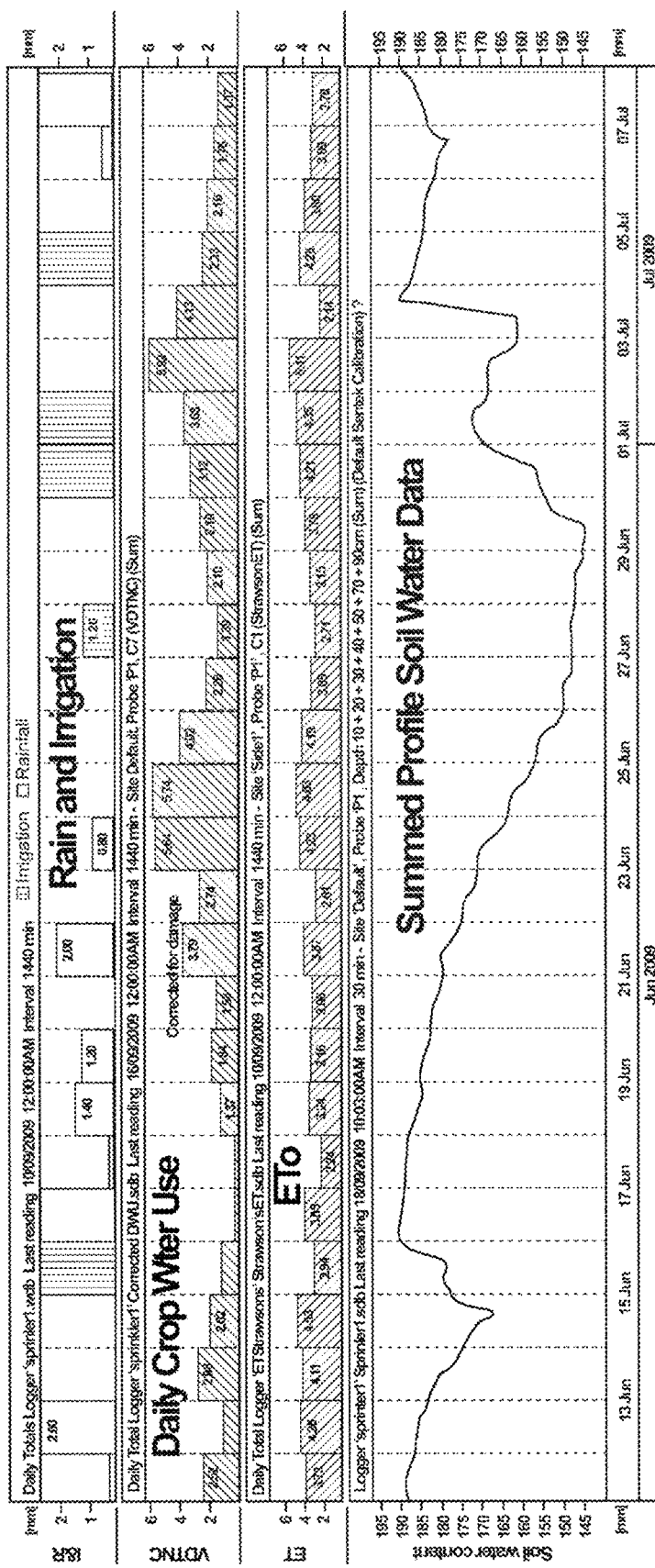
FIG. 11B depicts the groupings and comparisons of daily rain and irrigation event values, daily crop water usage, ETo values and summed profile soil water data obtained from an array of sensors in the vicinity of a plant crop and the occurrence of a soil water stress condition.
Figure 11C:
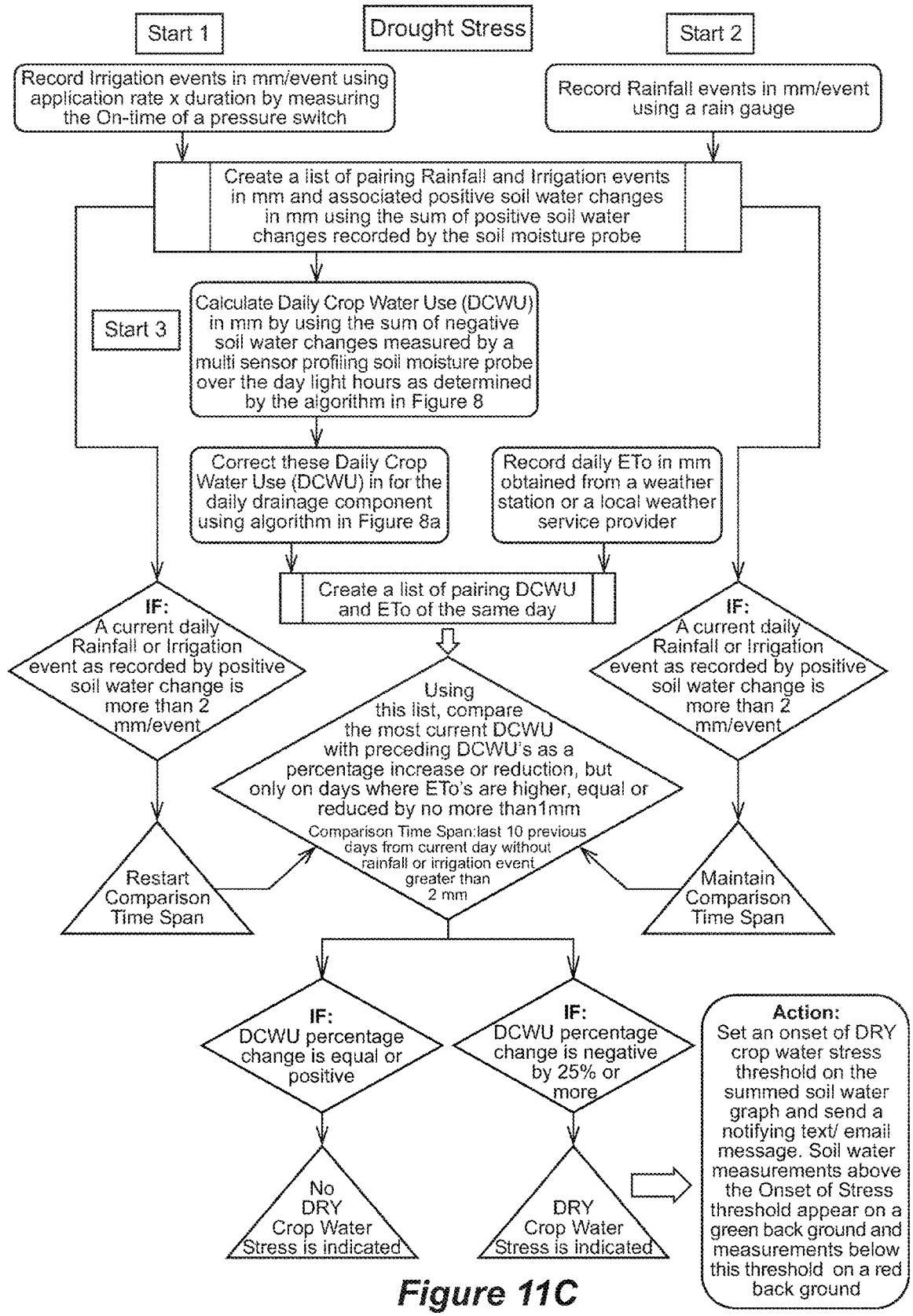
FIG. 11C is illustrative of a flow diagram of the steps of assessment of soil water stress (drought) conditions.

Various example steps and rules to make an assessment of the onset of water stress of the crop are an embodiment of the various methods disclosed in this document, and pictorial examples illustrating an onset of water stress are provided by FIGS. 11B and 11C, and the assessment of the onset of water stress is depicted for the particular methods described in conjunction with those Figures. It will be appreciated that the ability to measure the relevant DWU is reliant on the methods of analysis of the water moisture recordings of a sensor array, which are as described by way of example only, previously described in this disclosure and noting that the relevant sensors can be co-located with the soil moisture sensor array. Noting that capacitive sensors used in an array are but one example of a suitable soil moisture measurement sensor technique and as are the various arrangements for determining water in soil events and the ETo.

Figure 11D:
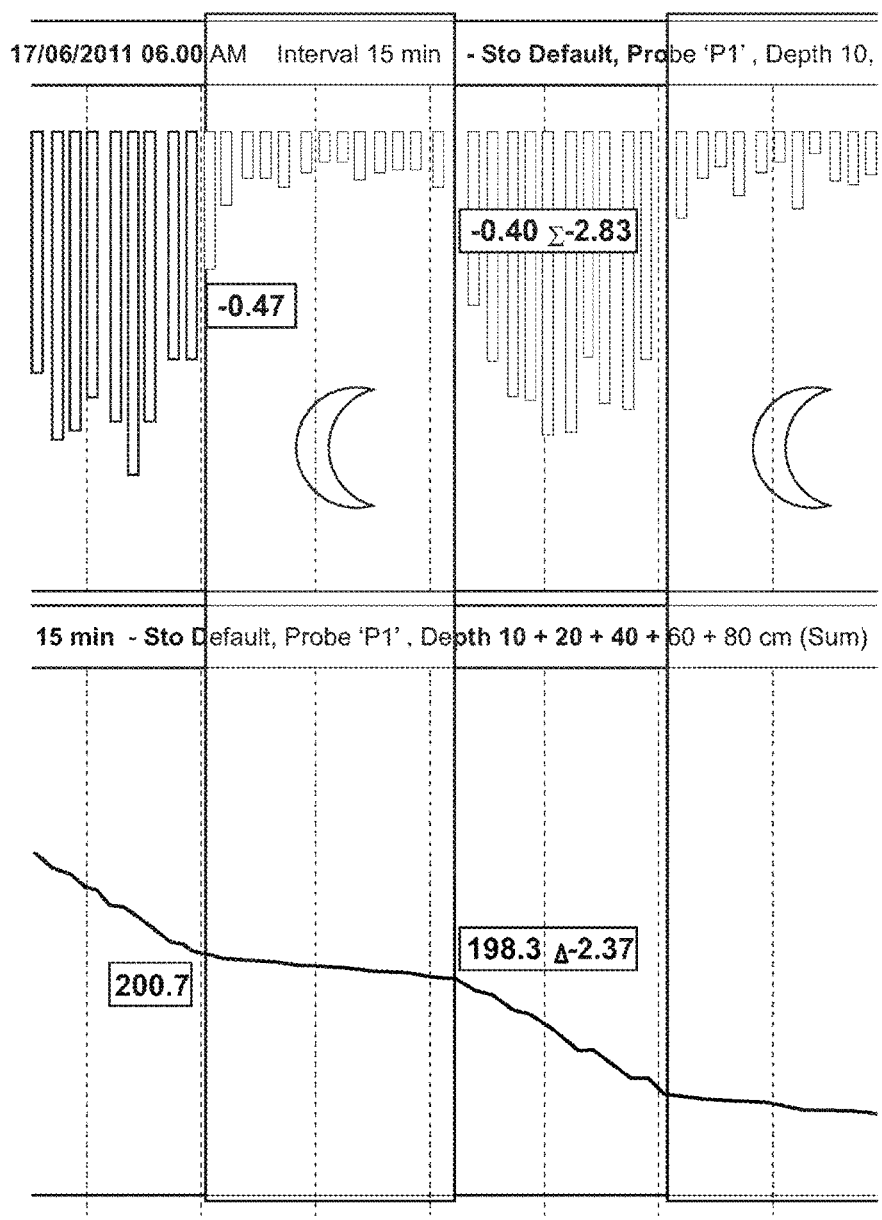
FIG. 11D depicts a correction accounting for the drainage component.

FIG. 11D depicts the time zones of the day during which the water is moving through the soil profile without the effect of plant water take-up. In this depiction there is an overall reduction in the total soil water measured by the soil moisture sensor. However, there can be situations which reflect the movement of soil water such that there is an increase during those time zones, which can be caused by the water accumulating in the under-brush of the crop and then during the time zones indicated re-entering the soil and filtering downwards but still accounted for in the cumulative sensor values measured by the array of soil sensors. In either event, it is necessary to accommodate for the movement in the Daily Corp Water Use values used in the calculations associated with the methods described herein. VDTNC=Corrected Daily Crop Water Use is the DayTime-NegChange (for this illustration)−((DayTimeHours/NightTimeHours)*NightTimeNegChange).

Figure 12:
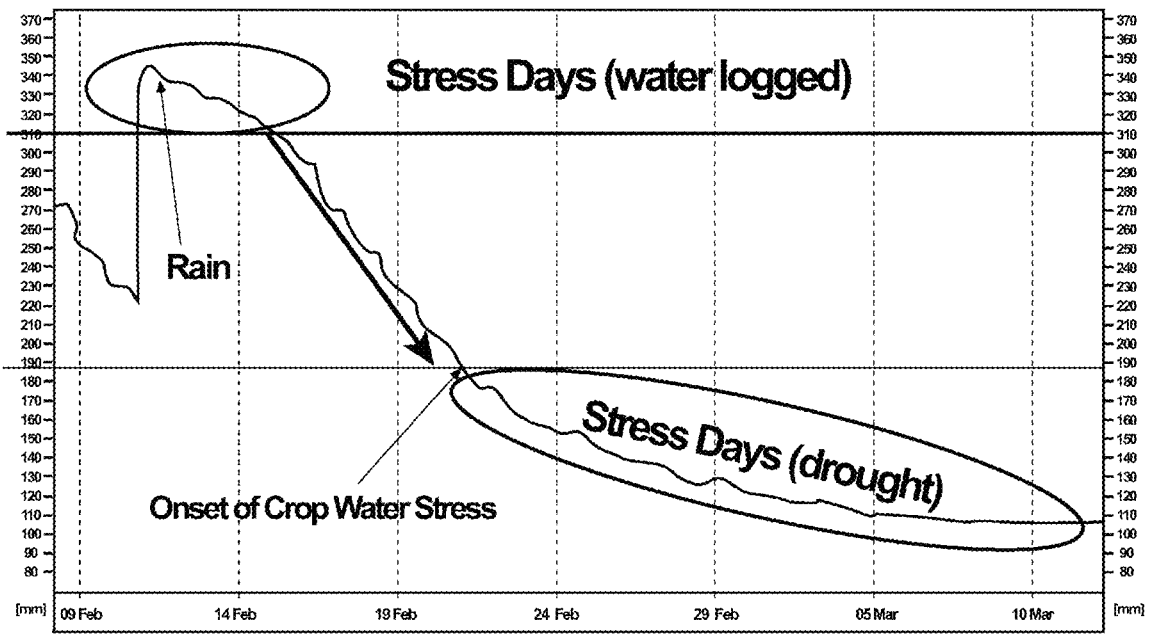
FIG. 12 depicts an illustration of soil water stress conditions including a water restricted condition.

FIG. 12 illustrates that the graphical characteristics of water stress of a crop and the following steps are one embodiment to determine when that stress began when the following inputs are available.

Inputs:

Daily Reference ETo in mm (from a weather station, BoM or any other Internet weather service provider).

Daily Crop Water Use (DWU in mm/100 mm), which in one embodiment may be corrected for the drainage component based on the default calibration equation measured by the soil water probe/sensor.

Water in soil events (irrigation, rainfall) in mm measured by a water in soil detector arrangement and by way of example only, such an arrangement can be a soil water probe or even an above ground water gauge located near the soil moisture sensor, each having not only a water detection sensor but at least an output representative of the water in soil event. The quantity of water in the soil or that which has been detected before it enters the soil (as in a rain gauge) is not as important as having an output that represents that there has been water which would be expected to enter the soil. However, in an arrangement the quantity of water is gauged. The arrangement is importantly used to discount that particular day as a contributor to the history of the water uptake of the crop/plants. It can be that the water in soil detector arrangement is also the soil moisture detection arrangement or it could be a separate arrangement. It is the soil in water detection output that is useful for the methods described in this specification.

Step 1:

Each day record prevailing ETo in mm and DWU (corrected) in mm (the correction mentioned will be described in relation to an adjustment to account for the natural effect of water draining down into the soil that occurs all the time but predominantly during the hours not being water take-up hours, which tend to coincide with non-day-light hours of the day).

Step 2:

Each day during the course of a soil drying cycle, which is not a day during which there is a soil wetting event, also referred to as a water in soil event (rain or irrigation event), assign the prevailing ETo to a 1 mm ETo range or bracket. For example only, as there are other ways to make comparisons between ETo levels from day to day, say an ETo of 6.3 on day X mm belongs to the ETo bracket 6.1-7 mm ETo. The assignment of an exact ETo reading to a range of ETo readings is conducted to allow for comparison of what will be deemed to be the same/similar ETo days. Thus the choice of range is a matter based on experience and knowledge of the characteristics of ETo in the field. An ETo on day Y of 5.7 is thus allocated to an ETo bracket 5.1-6 mm etc. Thus it is one consideration to create sufficient ETo brackets to cover the seasonally encountered range of ETo's. In another example, a percentage variation between one ETo and another can be used, say within 20% difference, again this % is chosen based on the seasonally encountered range of ETo's.

Step 3:

Thus in one example, the ETo of each recorded day 1 is allocated to a particular ETo bracket associated with a measured DWU. During a soil water drying cycle, after an irrigation or rainfall event, a number of ETo brackets will be created. Each subsequent day will generate either the same numerical ETo bracket or a new numerical ETo bracket.

Step 4:

During a soil water drying cycle DWU's are compared only within the same occurring ETo bracket starting from the date after an irrigation event. Each passing day will generate a new ETo bracket with an associated DWU that can be compared with DWU's from same ETo bracket days that have occurred earlier in the drying cycle. Days during the course of a soil drying cycle where any soil re-wetting event occurs (no matter how small) will be excluded in the backward comparison of DWU in the same ETo brackets, in other words no percentage reduction calculations of DWU will be performed.

Step 5:

DWU's of an ETo bracket and the next same numerical occurring ETo bracket will be compared on the basis of a percentage reduction in DWU from the first bracket occurrence to the next same numerical bracket occurrence. Example; ETo bracket is 4.1-5. DWU on the first day is 3.96 mm. The next occurrence of this 4.1-5 ETo bracket happens 2 days later. The DWU on this day is 2.61 mm. This means that the DWU value has dropped 65.90% compared to the DWU recorded on the first same ETo bracket day 2 days ago. This is a drop of 34.09%.

Step 6:

If the percentage reduction of soil water usage measured between DWU's on subsequent same ETo bracketed values days equals or exceeds, a predetermined reduction, say 30% reduction, then in the view of the developer the onset of water stress is indicated. It can thus be said that the crop has encountered a problem in drawing soil moisture from the soil despite the environmental conditions on an earlier day being similar when it is shown by the representative data that there was a greater volume of moisture drawn from the soil. The difference exists when it would be expected that there should be the same or a similar draw of moisture from the soil. As depicted in FIG. 11B DWU data having the characteristic below this threshold can be graphed using a hashed background, wherein the top level is drawn across the graphical representation of the soil moisture levels at the various times those levels were measured and it would also suffice to just show a line labelled "Onset of Stress". A 30% reduction between DWU's on comparable days can be used to indicate approaching onset of water stress. Data below this threshold would be graphed using a coloured background (not shown). The water extraction of a plant under very similar atmospheric demand or ETo conditions (varying over a range of 0.9 mm), shows a 20 or 30% percent reduction in plant water uptake, with measurement events being from 1 to 5 days apart. In another example, positive percentage values (if none of the preceding values are >30%) would indicate an increase of DWU in the latest comparison and not be indicative of crop water stress.

Step 7:

If there is a lack of the same ETo bracket days to compare going back as many as 12 days, DWU's of a lower ETo bracket day can be compared to DWU's recorded on higher ETo bracket days. If the DWU on a higher ETo bracket day is the same or lower compared to a preceding lower ETo bracket day within 12 days, then the onset of crop water stress is indicated.

Step 8:

If there is a soil re-wetting event, the onset of stress assessment will restart its calculations from that event/point onwards and ignore ETo brackets before that re-wetting event. In the view of the developer a re-wetting event is enough to affect the method such that that day is discounted and the DWU is ignored for that day, but it does not prevent the comparison of DWU's in previous ETo brackets.

Step 9:

If diurnal fluctuation of soil water is observed (soil water rise during day time due to vapour pressure deficit increases above the soil surface) then calculation of DWU will use the difference in mm between the lowest soil water records of the day.

Step 10:

If there is no difference between the soil water depletion rates at night, with the day, the assessment will not calculate the onset of stress point.

FIG. 11C is illustrative of a flow diagram of the steps described above.

Calculate the day light hour Daily Crop Water Use (DCWU) corrected for drainage using the sum of negative or sometimes positive soil water change over the soil profile to be measured. Compare the most current DCWU with preceding DCWU's as a percentage increase or decrease on days where ETo values are higher, equal or less by no more than 1 mm. The comparison time span for this evaluation is the last 12 days from the current day without positive soil water profile change events in that period that are greater than 2 mm. Soil water profile change events that are greater than 2 mm will trigger a restart of the comparison time span. If the most current DCWU percentage change is equal or positive, no drought (DRY) water stress is indicated, but if the DCWU percentage change is negative by 30% or more then drought (DRY) crop water stress is indicated.

The use of at least 12 days in the example provided is but one of many periods, the user of the system can be provided the ability to select a different period since there can be determinants such as crop type, soil type, ETo ranges and other weather related reasons such as humidity and arid environments to lengthen or shorten the relevant period. Thus, for example, for crop that grows very quickly the period may be shortened, for a crop that grows very slowly the period may be lengthened. For a region that experiences a very large variation of ETo values over a daily period then a larger than 1 mm range may be used, such as may be the case in Saudi Arabia, while a very limited ETo range may require the use of a very much less range than 1 mm, such as may be the case in England. The ETo value may also be affected by the season and thus adjustment of the ETo range can be made to suit. Yet further, the use of a 30% decrease as the measure for when crop stress is indicated may be varied for where the crop growth rate is entering a particular period or the crop growth rate, for example when it is low the % may be set lower or higher as the case may be.

The user will typically be provided a pre-set of the various values but it will also be possible for the user to gain experience in the use of the method and associated apparatus to make their own assessments or be advised of the most appropriate values.

Figure 13:
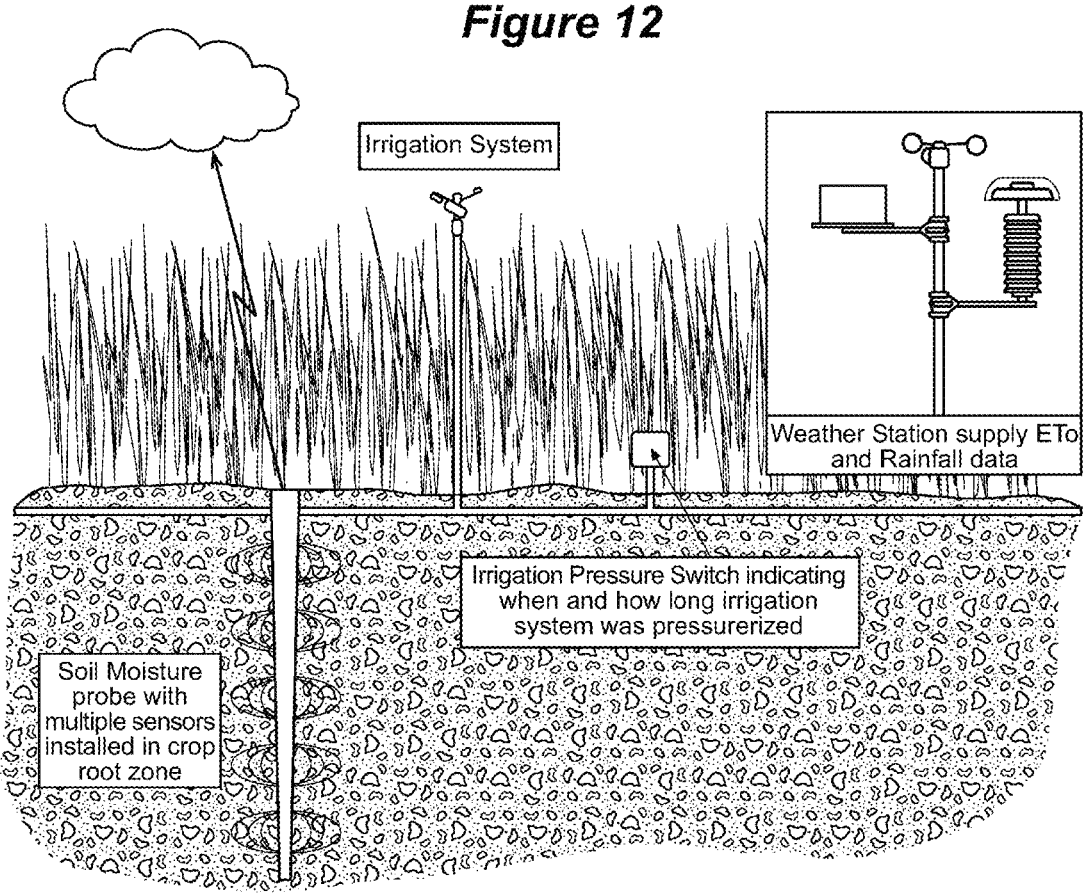
FIG. 13 depicts a system for collecting and analysing soil moisture values, ETo and monitoring and control of irrigation arrangements.

FIG. 13 depicts a system for collecting and analysing soil moisture values, ETo, water into soil events (rain/irrigation water gauge), and control of irrigation arrangements. The system includes a soil moisture sensor array as described herein, providing soil moisture measurements as described. The analysis of those measurements and other data, such as, the rain/irrigation gauge readings (including the most basic indication of a water into soil event even without the level of that infiltration), the ETo (or elements that allow the ETo to be determined as collected from apparatus such as temperature, wind speed, vapour content, etc.) can be performed within the soil moisture sensor array and further wherein the sensor array is also adapted to receive externally obtained data, such as ETo from a digital cloud based server, the sensor arrangement can receive the relevant data from one or more sources, such as the BoM. The system also includes in an embodiment a processor and associated digital data memory for performing one or more of the algorithms described in this specification. The processor and associated digital data memory can be located anywhere as long as there are communication paths via one or more known data communication networks (the details of the data communication networks are not part of the detailed knowledge which is required to implement the system). The various algorithms described in this specification can be expressed in digital data code according to best practice known to those of skill in that art and executed in the processor from their storage location in volatile or non-transitory digital data memory devices. The output control of, say an irrigation valve to initiate a predetermined water in soil event over the one or more crop plants, can in one embodiment, be directly connected to the valve from an output of the processor, or provided from a remote processor and associated digital data memory arrangement via the same or different communication networks to the valve. The network aspects of the system are known to those of skill in that particular art. The use of Software as a Service arrangements provide for the execution of the required software, collection of the various representative data, determination in accordance with the various algorithms described and the provision of an output suitable for adaption to control one or more aspects of the system, in particular the control of the supply of water for a water in soil event to the one or more plants.

The output of the analysis can be used to operate water in soil events, such as an irrigation system by operating values which control the supply of water to an irrigation water distributor and it may control valves and associated pumps to distribute fertiliser, and an array of crop condition changing devices.

The irrigation system can have many locally measured inputs as well as inputs obtained from remote resources (tanks, reservoirs, lakes, etc.), and have controls which allow the water in the irrigation system to be controlled by where, when and how much is used to irrigate the crop, with key characteristics being monitored locally or remotely.

The outcome of analysis in accordance with the methods described herein allow for the operation of the irrigation system to provide water to the crop in response to a determination of soil water crop stress, or in circumstances of over water stress to a crop, to restrict water in soil irrigation events. A further possible output to indicate the stress condition of the crop is the provision of a human readable alert or an alert suitable to be detected by a sense of a person, who is responsible for the management of the crop. The alert may prompt the person to review the irrigation program for the crop, the planned and prior use of fertiliser, and other crop inputs.

Figure 14:
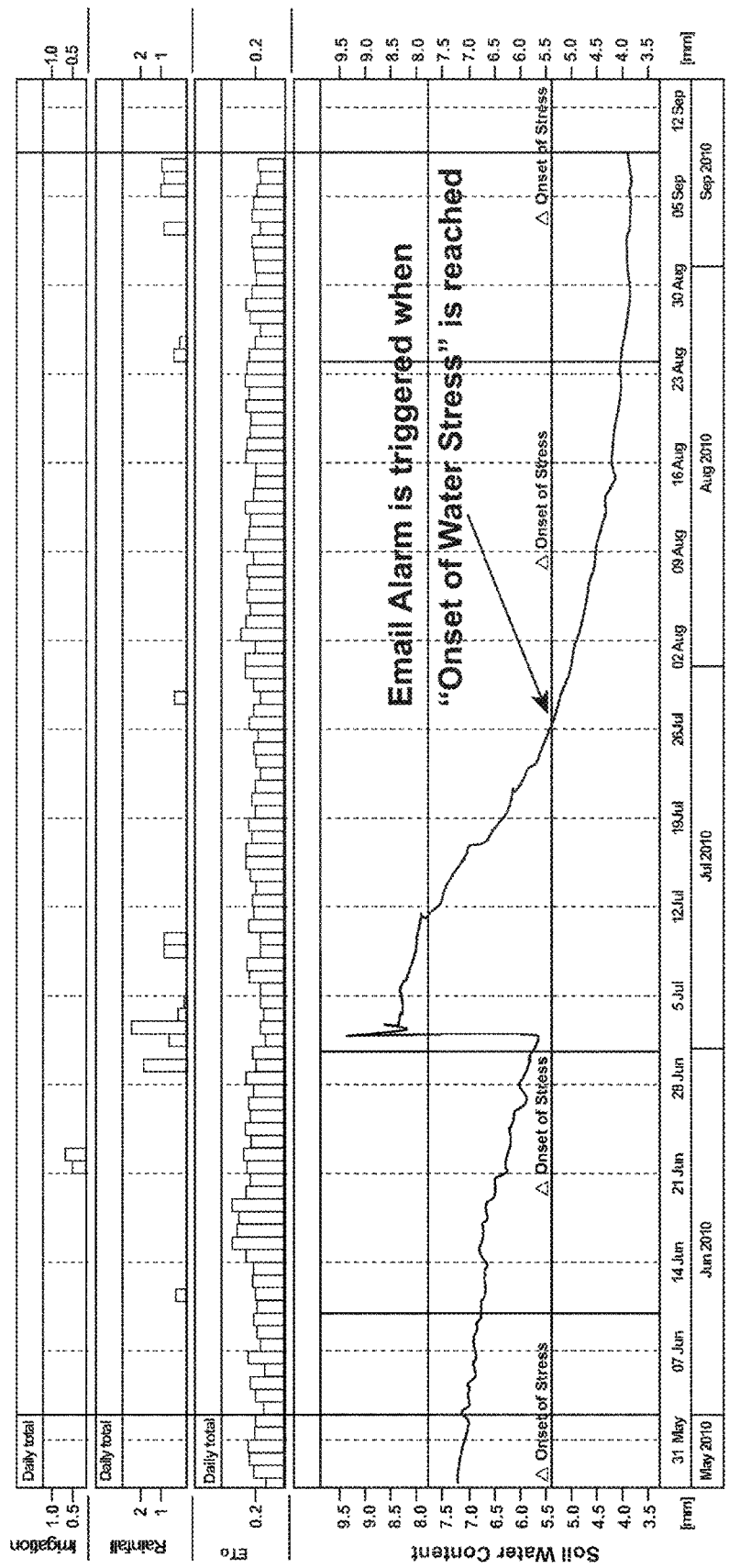
FIG. 14 depicts a direct consequence of the analysis of various characteristics of soil moisture and environmental measurement.

FIG. 14 depicts a direct consequence of the analysis of various characteristics of soil moisture and environmental measurement, being an alert at the onset of stress. The analysis can be used not only on live data generated in the past days but it can also be used to analyse historical data and to then correlate that data with crop yields and other indicators of crop health to better understand the relationship between soil moisture availability, crop health, and growth.

Figure 15:
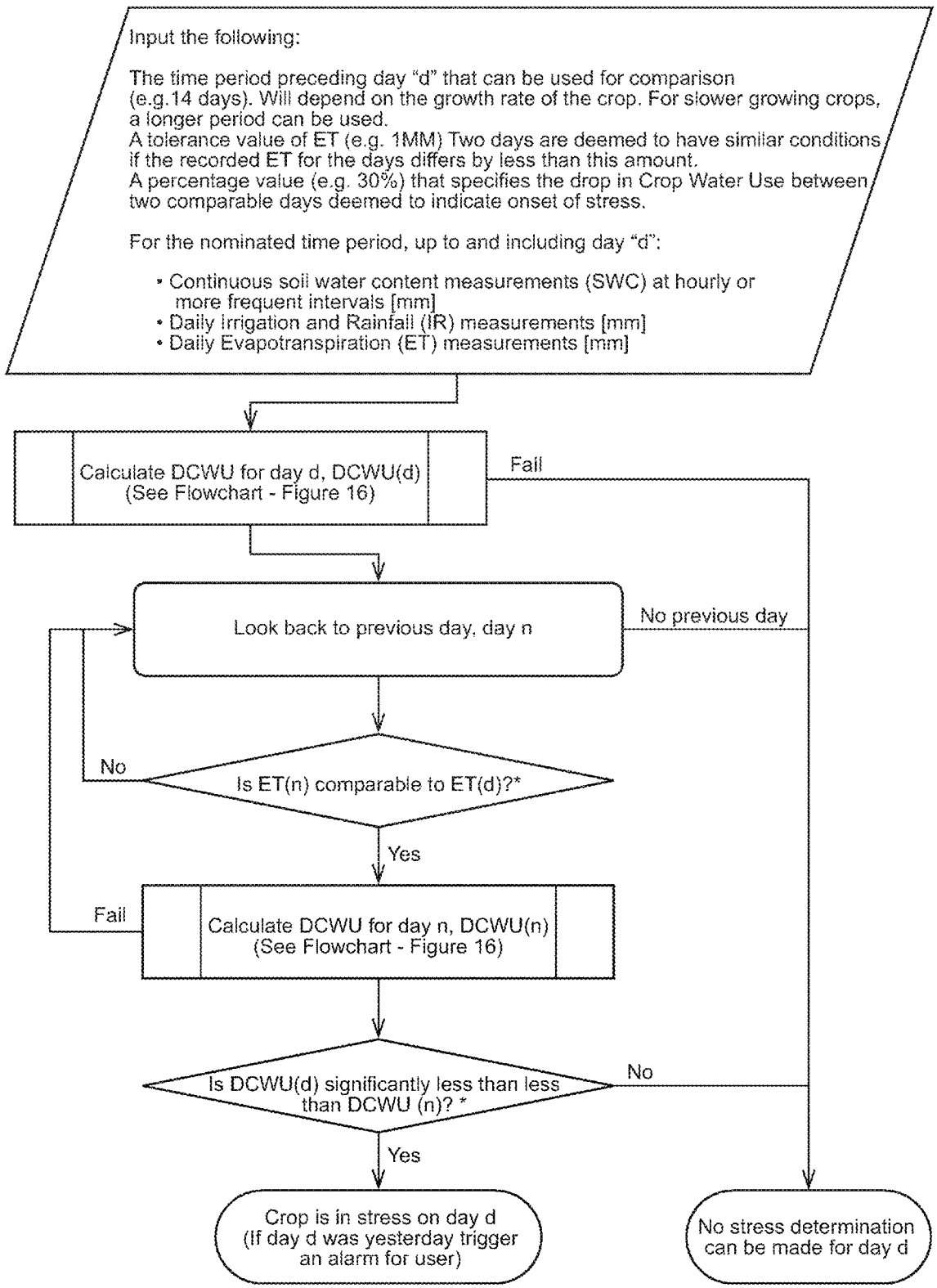
FIG. 15 depicts an exemplary method to determine whether there is a plant stress on a given day d.

FIG. 15 depicts a further exemplary method to determine whether there is a plant stress on a given day. In this example, data collected from the start of relevant data, up to and including day d is input into the method. The data available includes the following information:
   a. Soil water content measurements (SWC) at hourly or more frequent intervals [mm]
   b. Daily Irrigation and Rainfall (IR) measurements [mm]
   c. Daily Evapotranspiration (ET) measurements [mm]

Based on the data, the Daily Crop Water Use (DCWU) is calculated for day d. An example of how DCWU is calculated is presented in FIG. 16. If the calculation fails, then it would be determined that it is not possible to make a stress determination for day d. If the calculation returns a result, the next step is to look back to the previous day (day n) then compare the ETo of day n to ETo of day d. If the ETo (day n) and ETo (d) are not comparable, the step of looking back to the previous day is performed again (in essence the first day n and day d-1 is the second day and day d-2 is the third day back, etc.). The ETo of the new day n is compared to ETo of day d again. At any time when ETo of day n is comparable to ETo of day d, the DCWU of the corresponding day n is calculated. If calculation of DCWU of day n fails to return a result, the step of look back to the previous day is performed again. If DCWU produces a result, then the DCWU of day d is compared with DCWU of day n so as to determine whether DCWU of day d is significantly less than DCWU of day n. If it is significantly less (the level is disclosed elsewhere in this document but by way of example if the level is less by 30%), then it would be concluded that the crop is in stress on day d. If not, the step of looking back to the next previous day is performed again. The loop of going back to the step of looking back to the next previous day is broken once the step has been performed a predetermined number of times (say 12 times).

For the above, comparable ETo means the difference is less than a predetermined threshold value. In one embodiment, the difference is less than 1 mm. Depending on crops and environmental factors etc., the difference can be less than 0.8 mm, 1.2 mm, 2 mm etc. to be considered comparable. For the above a DCWU value is determined to be 'significantly less' than another if it is less than a predetermined fraction or percentage of the other. In one embodiment, the 'significant less' means lesser than 75% of the other. Again, depending on crops and environmental factors etc., the fraction or percentage can be changed to another suitable value. It is also possible to compare ETo's by allocation of an ETo to bands and if two ETo's are within the same band then they are comparable.

The following is an example of pseudo code for implementing one form of the method:
   To determine whether there is plant stress on day d
   Is rainfall/irrigation/ET data available for day d? No>Fail
   Is rainfall/irrigation less than 2 mm on day d? No>Fail
   Does stepping detection method identify period of daytime plant water uptake on day d? No>Fail
   Calculate water loss (due to drainage) outside period of plant water uptake on day n, and subtract proportionally from the amount of plant water uptake, to provide daily crop water use adjusted for drainage DCWU(d)
   Is DCWU(d) a positive value? No>Fail Now Loop descending backward through earlier days as n:

Have we already looped through 10 earlier days? Yes>Break loop and fail

Is rainfall/irrigation/ET data available for day n? No>Continue loop

Is rainfall/irrigation less than 2 mm for day n? No>Continue loop

Does ET(n) differ from ET(d) by less than 1 mm? No>Continue loop

Does stepping detection method identify period of daytime plant water update on day n? No>Continue loop Calculate daily crop water use adjusted for drainage for day n, DCWU(n)

Is DCWU(n) a positive value? No>Continue loop

Is DCWU(d) less than 75% of DCWU(n)? No>Continue loop

Plant water stress is indicated. Finish.

Figure 16:
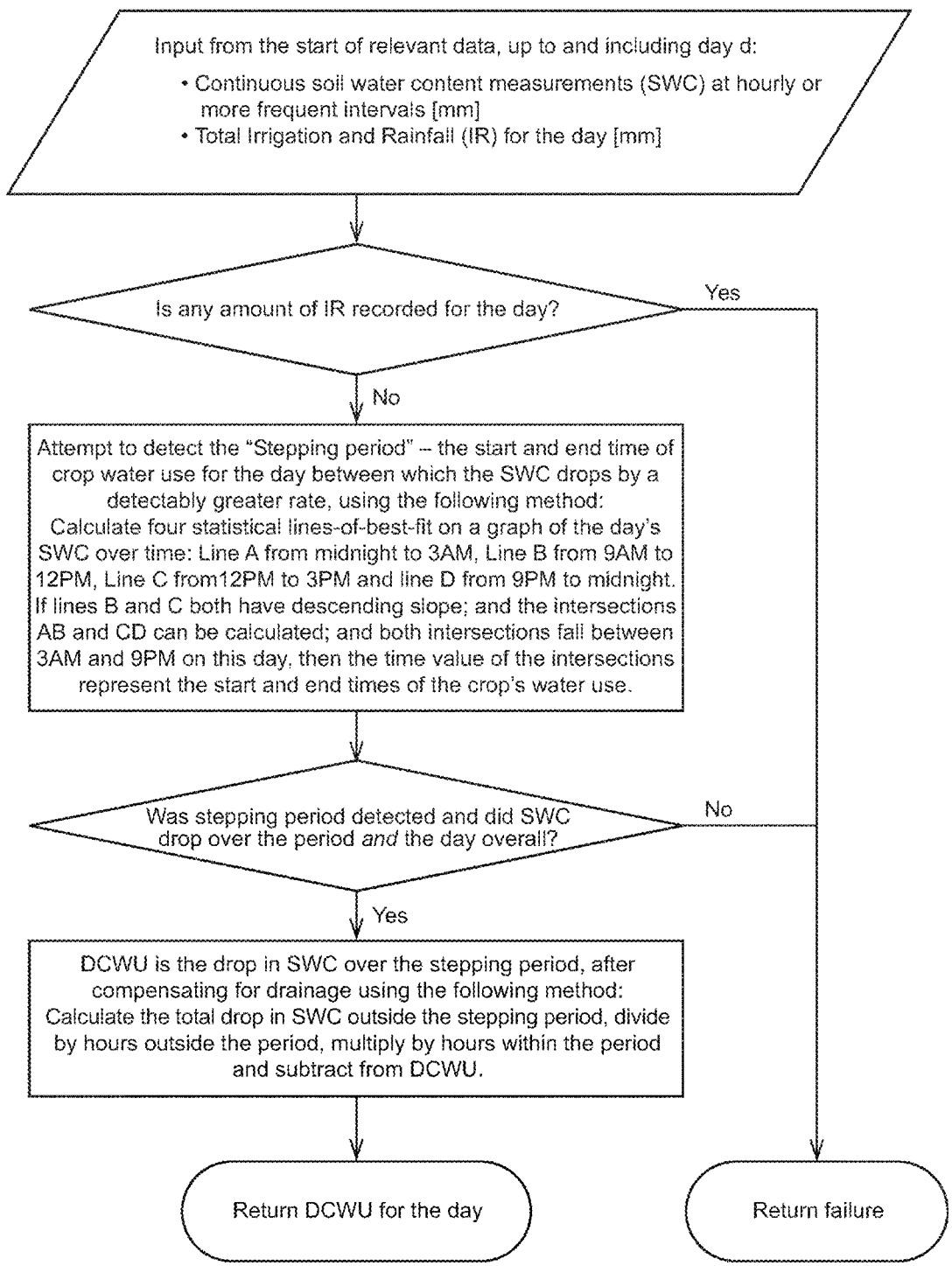
FIG. 16 depicts an exemplary method to calculate daily crop water use for a given day.

FIG. 16 depicts an exemplary method to calculate daily crop water use (DCWU) for a given day. In this example, two inputs are required, namely:

d. Continuous soil water content (SWC) for the day at hourly intervals or more frequently [mm]; and e. Total Irrigation and Rainfall (IR) for the day [mm] or at least an indication of a water in soil event so that the method will discount the day that event occurs on.

With these inputs, the next step is to test whether the IR has occurred.

If IR is detected, the calculation fails, for example, by returning an error code. If IR is small enough, the next step is performed, during which there is an attempt to detect the "Stepping period" (the start and end time of crop water use for the day between which the SWC drops by a detectably greater rate), using the following method:

Calculate statistical lines-of-best-fit for the data collected from the soil moisture sensor array as described elsewhere in this disclosure (it is helpful to use a graphical tool to conduct this analysis, however, the representative data collected can be used as well) of the day's Soil Water Content over time: for a first of the respective 24 hour periods is used to:

Determine a first rate of change of the consecutive or extrapolated summed values of soil moisture content in mm/100 mm over a period of at least the period midnight to 3 am;

Determine a second rate of change of the consecutive or extrapolated summed values of soil moisture content in mm/100 mm over a period of at least the period 9 am to midday;

Determine a third rate of change of the consecutive or extrapolated summed values of soil moisture content in mm/100 mm over a period of at least the period midday to 3 pm;

Determine a fourth rate of change of the consecutive or extrapolated summed values of soil moisture content in mm/100 mm over a period of at least the period 9 pm to midnight;

Determine the plant related rate of change of the consecutive or extrapolated summed values of soil moisture content in mm/100 mm over a period at least 2 hours either side of noon of the respective 24 hour period;

if and only if the second and third rates of change are negative determine a first time of day intersection of the first rate of change with the second rate of change and a second time of day intersection of the third related rate of change with fourth rate of change;

if and only if the first time of day and second time of day fall within 3 am and 9 am the first time of day and the second time of day represent respectively the nominal start and end times of the day of water use by the crop being the plant moisture uptake period;

Determine the degree of the reduction of the plant related water use during the respective plant moisture uptake period by noting the soil moisture level at the beginning and end of the plant moisture uptake period and taking one value away from the other to determine the total measure (in mm/100 mm).

The determined value is indicative of the soil moisture take-up of the plant but the value is affected by the natural effect of soil moisture migration down into the soil and the method for determining this component for drainage over the total 24 hour day is calculated by determining the total drop in plant related water use outside the total plant moisture uptake period. It is then possible to divide that value by the remainder of the 24 hour period of the day not being the total plant moisture uptake period, and then multiply the result of the division by the plant moisture uptake period and subtract the result of the multiplication from the determined reduction of the plant related water use during the respective plant moisture uptake period to determine the compensated planted related water usage.

If one or both of conditions of (a) "Stepping period" is detected; and (b) SWC drops over the period and the day overall, are not fulfilled, then the calculation fails, for example, by returning an error code.

If both conditions are fulfilled, then the next step is to compute the DCWU. DCWU is the drop in SWC over the "Stepping period", after compensating for drainage.

Once computed, the DCWU is provided as the result of this method and can be compared to determine whether the rate of soil moisture depletion during the plant moisture uptake period within each respective 24 hour period reduces by a pre-determined level compared to the other of the respective 24 hour period.

Having made the determination it is possible to indicate the most recent of the respective two 24 hour periods as a period of water stress of one or more of the plants.

Figure 17:
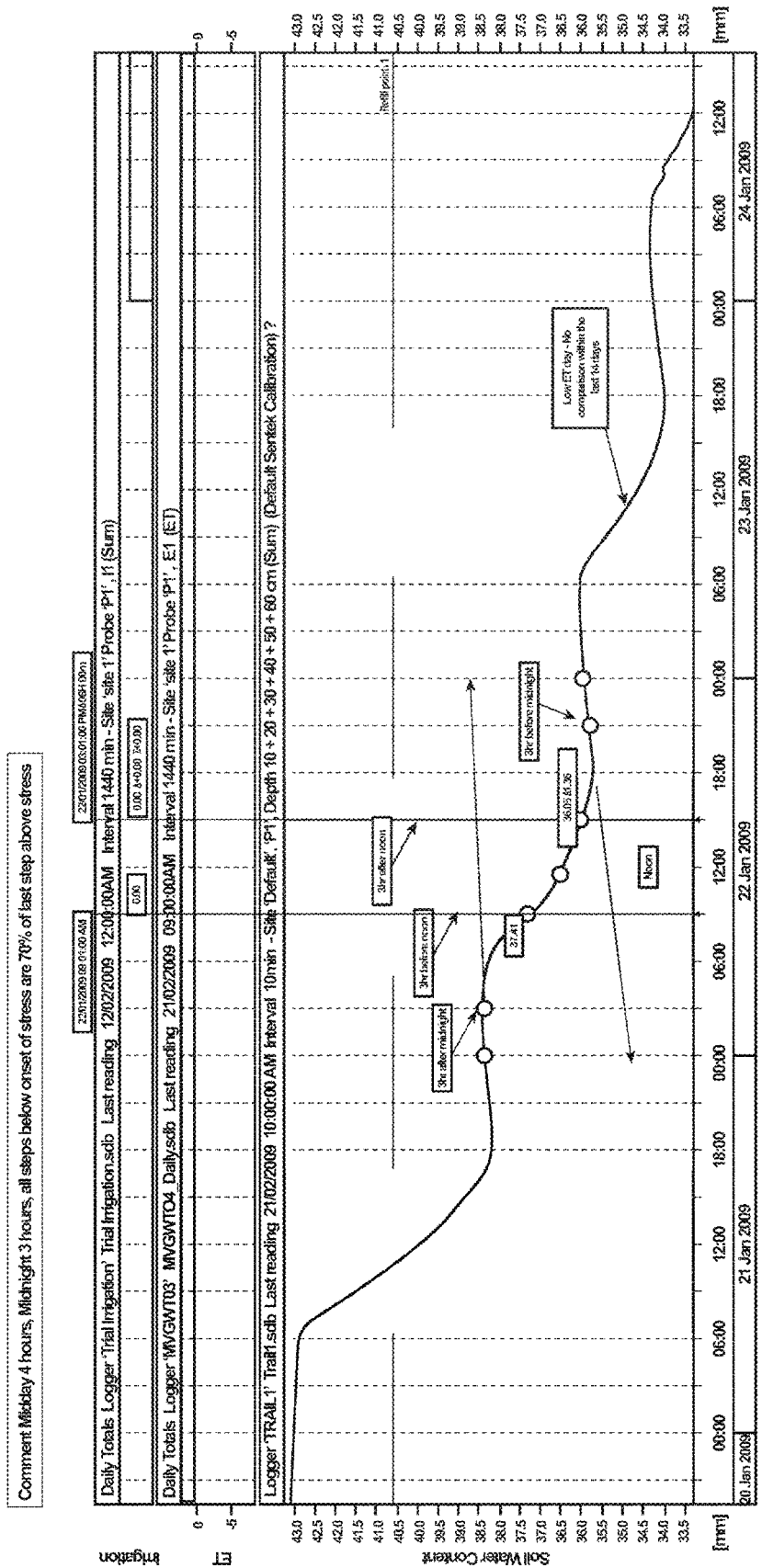
FIG. 17 graphically illustrates the process of identifying the rate of change of soil water uptake and water migration by identifying the period during which the plant is actively taking up soil moisture.

FIG. 17 graphically illustrates the process of identifying for a user the rate of change of soil water uptake and water migration. The data that creates the black line that extends from the top left hand corner of the graph to bottom right hand corner is the soil water moisture values determined as described previously over nearly a five day period. The vertical axis of the graph is soil moisture content in mm/100 mm and the horizontal axis is time with a six hourly indicator. For illustrative purposes the 24 hour period denoted 22 Jan. 2000 is used to show how the various rates of soil moisture depletion are determined. In the description to follow there is mention of the use for extrapolated summed values of soil moisture content, this requirement may arise if the intervals between soil moisture measurements are far enough apart to require intermediate values to be interpolated by one of many known techniques. The resulting representative data is thus a mixture of actual and interpolated values. However, seeing as the measurements are periodic in the first instance and not continuous then it follows that the representative data is exactly that, representative of the soil moisture level.

Determine a first rate of change of the consecutive or extrapolated summed values of soil moisture content in mm/100 mm soil depth over a period of at least the period midnight to 3 am and the upward (positive) slope of that rate of change is shown by the upper red arrow.

Determine a second rate of change of the consecutive or extrapolated summed values of soil moisture content in mm/100 mm soil depth over a period of at least the period 9 am to midday and the downward (negative) slope of that rate of change is shown by the upper white arrow.

Determine a third rate of change of the consecutive or extrapolated summed values of soil moisture content in mm/100 mm soil depth over a period of at least the period midday to 3 pm and the downward (negative) slope of that rate of change is shown by the lower white arrow noting that the slope of the upper white arrow is greater than the slope of the lower white arrow, which can be further interpreted to mean that the soil moisture uptake by the plant was slower in the after-noon hours than in the pre-noon hours.

Determine a fourth rate of change of the consecutive or extrapolated summed values of soil moisture content in mm/100 mm over a period of at least the period 9 pm to midnight and the upward (positive) slope of that rate of change is shown by the lower red arrow.

Determine the plant related rate of change of the consecutive or extrapolated summed values of soil moisture content in mm/100 mm over a period at least 2 hours either side of noon of the respective 24 hour period to become representative of the rate of change for that day.

If and only if the second and third rates of change are negative determine a first time of day intersection of the first rate of change with the second rate of change and a second time of day intersection of the third related rate of change with fourth rate of change, which can be seen in this example to be 0500 hours till 1730 hours a total of 12 and a half hours of plant moisture uptake activity.

This particular determination can also be used to determine if there is stepping during that particular 24 hour period, that is the variation of soil moisture take-up by the crop is such that the crop exhibits a healthy response to the environment but particularly to its ability to take-up moisture from the soil, and is thus indicative of the performance of the crop to the moisture in soil conditions. It is not always apparent from a viewing of the graphical representation exactly what the line represents, whereas the slope analysis methods disclosed reveal the required detail.

It will be appreciated that the use of the second and third slope determinations respectively with the first and fourth slope determinations provide what is considered an accurate determination of the actual period of soil moisture uptake by the crop. It is recognised that there may be other methods to achieve this determination but for the method as a whole in the determination of whether a crop is entering stress the described method is fit for purposes, but it does not mean that the method described is the only way to make that determination of but one portion of the process.

Figure 18:
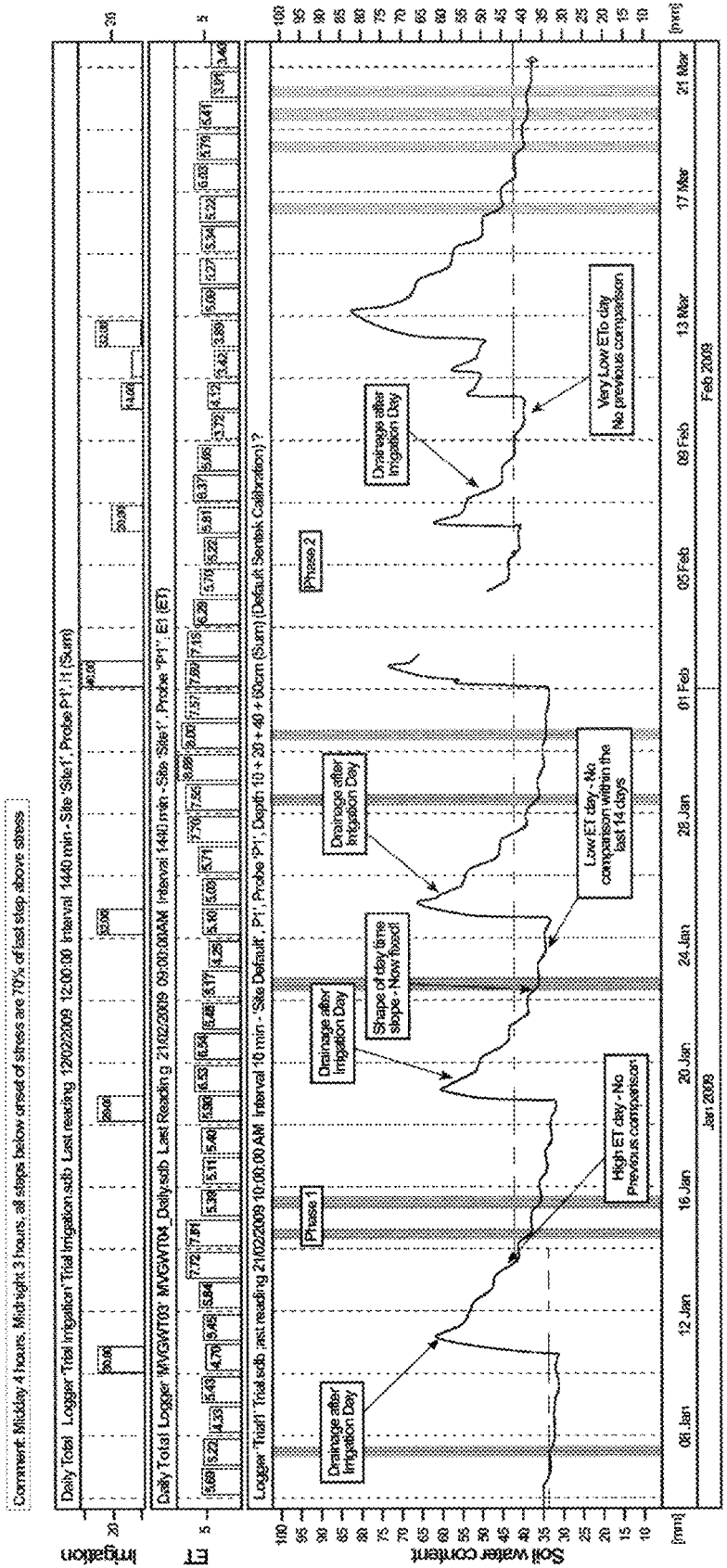
FIG. 18 graphically illustrates days of water stress and in particular the day when water stress begins.

FIG. 18 graphically illustrates days of water stress and in particular the day when water stress begins and achieves that by colour coding each day once the methods described herein are applied to the representative data for all the days illustrated, which extend from 6 January till 21 February (although the days between 1 February and 6 February are not illustrated as described herein). It should be noted that the illustration of a green band overlaying the nominal water uptake period of the 6th of January has been determined on the basis of representative data of earlier days (not shown), and likewise for the days following 7 January.

FIG. 18 also illustrates different looking bands, where the one band day is the onset of stress day and the following other bands are days of continuing stress. A third band type illustrates that the preceding day was one in which there was a water in soil event, which, is also shown by the further bands in the top most row which graphically illustrate the quantity of water involved in the water in soil event. The row of bands below the water in soil event row illustrates the ETo values of each day. The illustration graphically highlights the large number of days within the period of 18 days that the crop was in stress despite there being 8 water-in-soil events during the 47 day period.

Figure 19:
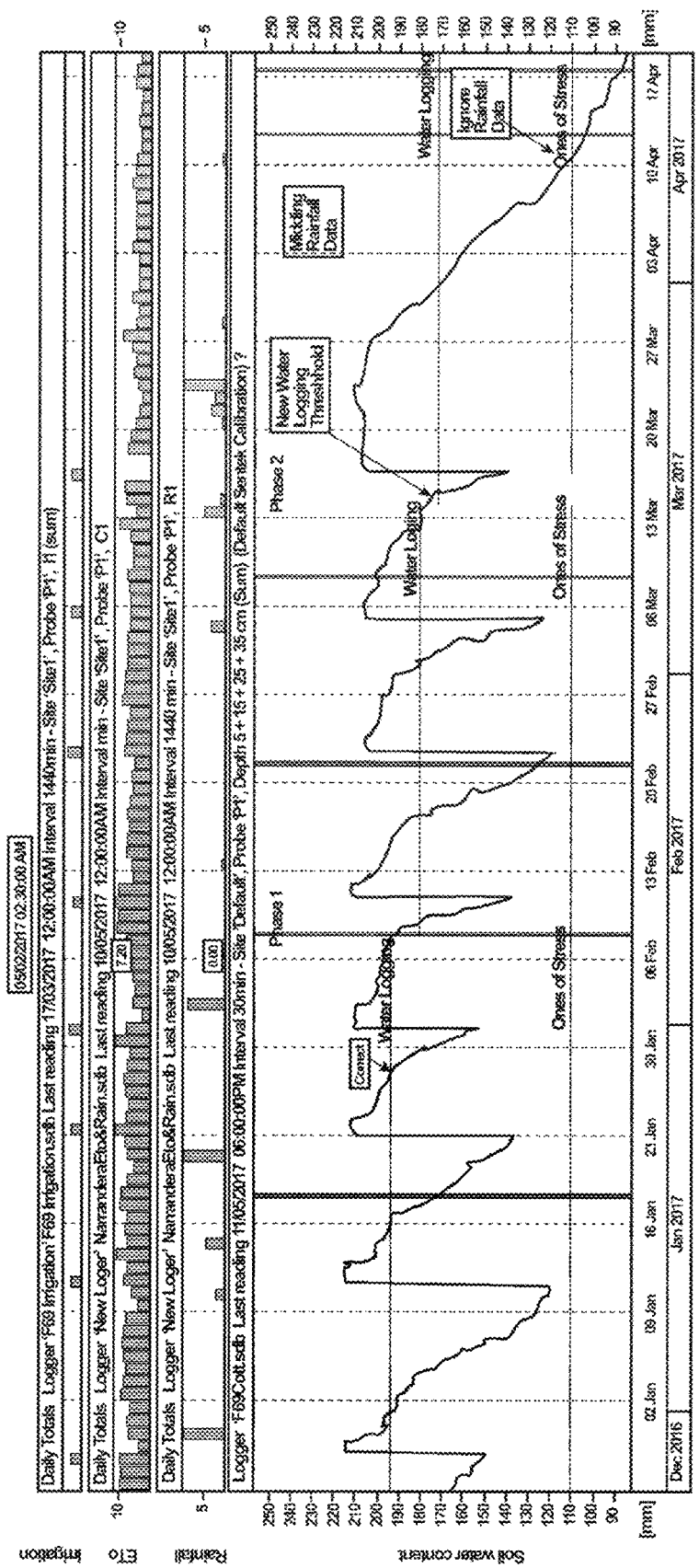
FIG. 19 graphically illustrates days of water stress and the days when those conditions begin.

FIG. 19 graphically illustrates days of water stress and the days when those conditions begin. The same band type scheme as described above in respect to FIG. 18 is used and the different band types of end points of the methods displayed in FIGS. 15 and 16, to indicate the different days at whether there was no stress (one shade), and day/s following a water in soil event an onset of stress day (another shade) and a day of continuing stress (a further shade). More particularly the crop is cotton which is flood irrigated and the graphical illustration reveals many days of water stress indicative of water being supplied to the crop on many occasions but less than would be optimum for crop health and growth.

Thus, as discussed in this disclosure, the methods applied to historical representative data can reveal a great deal about the crop condition and it then becomes a matter of further analysis to correlate the incidence of crop disease, crop fertiliser use, irrigated water use and other crop inputs and crop outputs such as quality and yields to explain the level of those outputs and how crop management may have been better handled. It is also discussed that the methods applied to current representative data can, if applied, daily provide a next day indication that the crop is entering a stress condition and that can be used by, for example, the crop manager to change their management processes, and/or allow the indication to control elements of crop management arrangement, such as for example, to irrigate or not to irrigate automatically with no human intervention.

The invention claimed is:

1. A method for indicating the onset of water stress in one or more plants located in a soil the roots of which are within the measurement zone of a vertical array of soil moisture sensors located in the soil to extend from the soil surface to at least below the root zone of the plants, the sensors adapted to provide representative data of the total water volume in millimeters of moisture per 100 millimeters of soil at multiple depths of the soil, at multiple times during a 24 hour period over a predetermined number of consecutive 24 hour periods, and representative data of the values of evapotranspiration within each of a maximum of fourteen consecutive 24 hour periods in the vicinity of the one or more plants is available, and a water in soil detector arrangement in the vicinity of the soil moisture sensors making available representative data of the event of a water into soil event within one or more of the consecutive 24 hour periods, wherein a plant moisture uptake period is a period of water use by the one or more plants, the steps of the method comprising:

a) determining from representative data there was no recorded water into soil event in the prior 24 hour period of a respective one 24 hour period;

b) determining from representative data whether there are two respective 24 hour periods of the prior seven consecutive 24 hour periods that also have evapotranspiration values within a predetermined range;

c) determining from representative data the rate of soil moisture depletion during the plant moisture uptake period within each respective 24 hour period adjusted for drainage;

d) determining whether the rate of soil moisture depletion during the plant moisture uptake period within each respective 24 hour period reduces by a pre-determined level compared to the other of the respective 24 hour period; and e) indicating the most recent of the respective two 24 hour periods as a period of water stress of the one or more plants, to thereby control elements of a plant management arrangement, to irrigate or not to irrigate automatically with no human intervention.

2. The method according to claim 1, wherein step f) comprises for a first of the respective two 24 hour periods of step b): determine a first rate of change of the consecutive or extrapolated summed values of soil moisture content in mm/100 mm over a period of at least the period midnight to 3 am; determine a second rate of change of the consecutive or extrapolated summed values of soil moisture content in mm/100 mm over a period of at least the period 9 am to midday;

determine a third rate of change of the consecutive or extrapolated summed values of soil moisture content in mm/100 mm over a period of at least the period midday to 3 pm; determine a fourth rate of change of the consecutive or extrapolated summed values of soil moisture content in mm/100 mm over a period of at least the period 9 pm to midnight; determine the plant related rate of change of the consecutive or extrapolated summed values of soil moisture content in mm/100 mm over a period at least 2 hours either side of noon of the respective 24 hour period; if and only if the second and fourth rates of change are negative determine a first time of day intersection of the first rate of change with the second rate of change and a second time of day intersection of the third related rate of change with fourth rate of change; if and only if the first time of day and second time of day fall within 3 am and 9 am the first time of day and the second time of day represent respectively the nominal start and end times of the day of water use by the the one or more plants being the plant moisture uptake period, wherein for a second of the respective two 24 hour periods of step b): determine a first rate of change of the consecutive or extrapolated summed values of soil moisture content in mm/100 mm over a period of at least the period midnight to 3 am; determine a second rate of change of the consecutive or extrapolated summed values of soil moisture content in mm/100 mm over a period of at least the period 9 am to midday; determine a third rate of change of the consecutive or extrapolated summed values of soil moisture content in mm/100 mm over a period of at least the period midday to 3 pm; determine a fourth rate of change of the consecutive or extrapolated summed values of soil moisture content in mm/100 mm over a period of at least the period 9 pm to midnight; determine the plant related rate of change of the consecutive or extrapolated summed values of soil moisture content in mm/100 mm over a period at least 2 hours either side of noon of the respective 24 hour period; if and only if the second and fourth rates of change are negative determine a first time of day intersection of the first rate of change with the second rate of change and a second time of day intersection of the third related rate of change with fourth rate of change; if and only if the first time of day and second time of day fall within 3 am and 9 am the first time of day and the second time of day represent respectively the nominal start and end times of the day of water use by the the one or more plants being the plant moisture uptake period.

3. A method according to claim 1 including compensating the soil water use by the the one or more plants for drainage over the total 24 hour day is calculated by determining the total drop in plant related water use outside the total plant moisture uptake period, and divide by the remainder of the 24 hour period of the day not being the total plant moisture uptake period, and then multiply the result of the division by the plant moisture uptake period and subtract the result of the multiplication from the determined reduction of the plant related water use during the respective plant moisture uptake period to determine the compensated plant related water usage.

* * * * *